US011236380B2

(12) United States Patent
Iverson et al.

(10) Patent No.: US 11,236,380 B2
(45) Date of Patent: Feb. 1, 2022

(54) METHODS FOR PREDICTING KINASE INHIBITOR RESISTANCE

(71) Applicant: Research Development Foundation, Carson City, NV (US)

(72) Inventors: Brent Iverson, Austin, TX (US); George Georgiou, Austin, TX (US); Joseph Desautelle, Austin, TX (US); Joseph Taft, Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 16/178,991

(22) Filed: Nov. 2, 2018

(65) Prior Publication Data
US 2019/0161787 A1 May 30, 2019

Related U.S. Application Data

(60) Provisional application No. 62/580,556, filed on Nov. 2, 2017.

(51) Int. Cl.
| | |
|---|---|
| *C12Q 1/48* | (2006.01) |
| *C12N 15/10* | (2006.01) |
| *C12N 9/12* | (2006.01) |
| *C12N 15/81* | (2006.01) |

(52) U.S. Cl.
CPC .............. *C12Q 1/485* (2013.01); *C12N 9/12* (2013.01); *C12N 15/10* (2013.01); *C12N 15/102* (2013.01); *C12N 15/1037* (2013.01); *C12N 15/81* (2013.01); *C12Y 207/10002* (2013.01); *C07K 2319/01* (2013.01); *C07K 2319/04* (2013.01)

(58) Field of Classification Search
None
See application file for complete search history.

(56) References Cited

U.S. PATENT DOCUMENTS

| | | | |
|---|---|---|---|
| 8,945,855 B2 | 2/2015 | Iverson et al. | |
| 9,546,359 B2 | 1/2017 | Iverson et al. | |
| 2009/0163510 A1 | 6/2009 | Lee | |
| 2015/0203834 A1 | 7/2015 | Iverson et al. | |
| 2017/0233781 A1 | 8/2017 | Iverson et al. | |

FOREIGN PATENT DOCUMENTS

WO  WO/2016/061199  4/2016

OTHER PUBLICATIONS

Arber et al., "s-cyclophilin is retained intracellularly via a unique COOH-terminal sequence and colocalizes with the calcium storage protein calreticulin," *J. Cell Biol.*, 116(1):113-125, 1992.

Benatuil et al., "An improved yeast transformation method for the generation of very large human antibody libraries," *Protein Eng. Des. Sel.*, 23(4):155-159, 2010.

Boder and Wittrup, "Yeast surface display for screening combinatorial polypeptide libraries," *Nat. Biotechnol.*, 15(6):553-557, 1997.

Čopič et al., "Genomewide analysis reveals novel pathways affecting endoplasmic reticulum homeostasis, protein modification and quality control," *Genetics*, 182(3):757-769, 2009.

Denecke et al., "Plant and mammalian sorting signals for protein retention in the endoplasmic reticulum contain a conserved epitope," *EMBO J.*, 11(6):2345-2355, 1992.

Escalona et al., "A comparison of tools for the simulation of genomic next-generation sequencing data," *Nat Rev Genet.*, 17(8):459-469, 2016.

Espada and Martín-Pérez, "An Update on Src Family of Nonreceptor Tyrosine Kinases Biology," *Int Rev Cell Mol Biol.*, 331:83-122, 2017.

Gai et al., "Yeast surface display for protein engineering and characterization," *Curr. Opin. Struct. Biol.*, 17(4):467-473, 2007.

Han et al., "Self-assembled amyloid-like oligomeric-cohesin Scaffoldin for augmented protein display on the *Saccharomyces cerevisiae* cell surface," *Appl. Environ. Microbiol.*, 78(9):3249-3255, 2012.

Hegde and Keenan, "Tail-anchored membrane protein insertion into the endoplasmic reticulum," *Nat Rev Mol Cell Biol.*, 12(12):787-798, 2011.

Huang et al., "Conserved WCPL and CX4C domains mediate several mating adhesin interactions in *Saccharomyces cerevisiae*," *Genetics*, 182(1):173-189, 2009.

Huang et al., "Discovery of 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide (AP24534), a potent, orally active pan-inhibitor of breakpoint cluster region-abelson (BCR-ABL) kinase including the T315I gatekeeper mutant," *J. Med. Chem.*, 53(12):4701-4719, 2010.

Kim et al., "Construction of an in vitro trans-sialylation system: surface display of Corynebacterium diphtheriae sialidase on *Saccharomyces cerevisiae*," *Appl Microbiol Biotechnol.*, 88(4):893-903, 2010.

Kolaczkowska et al., "Compensatory activation of the multidrug transporters Pdr5p, Snq2p, and Yor1p by Pdr1p in *Saccharomyces cerevisiae*," *FEBS Lett.*, 582(6):977-983, 2008.

Levy et al. "Attacking a Moving Target: Understanding Resistance and Managing Progression in EGFR-Positive Lung Cancer Patients Treated With Tyrosine Kinase Inhibitors," *Oncology (Williston Park)*, 30(7):601-612, 2016.

Li et al., "Profiling Protease Specificity: Combining Yeast ER Sequestration Screening (YESS) with Next Generation Sequencing," *ACS Chem. Biol.*, 12(2):510-518, 2017.

Lin et al., "A novel fragment of antigen binding (Fab) surface display platform using glycoengineered Pichia pastoris," *J. Immunol. Methods*, 375:159-165, 2012.

(Continued)

*Primary Examiner* — Anand U Desai
(74) *Attorney, Agent, or Firm* — Parker Highlander PLLC

(57) ABSTRACT

Provided are methods for the identification of mutant kinases that are resistant to inhibition by a kinase inhibitor. In some embodiments, the methods may be used to assess a test compound or kinase inhibitor for the risk of the development of resistance in vivo, e.g., during clinical administration to treat a disease such as a cancer.

45 Claims, 10 Drawing Sheets

Specification includes a Sequence Listing.

(56) References Cited

OTHER PUBLICATIONS

Park and Rapoport, "Mechanisms of Sec61/SecY-mediated protein translocation across membranes," *Annu Rev Biophys.*, 41:21-40, 2012.
PCT International Search Report and Written Opinion issued in International Application No. PCT/US2018/058834, dated Jan. 28, 2019.
Rapoport, "Protein translocation across the eukaryotic endoplasmic reticulum and bacterial plasma membranes," *Nature*, 450(7170):663-669, 2007.
Seidah and Prat, "Precursor convertases in the secretory pathway, cytosol and extracellular milieu," *Essays in Biochemistry*, 38:79-94, 2002.
Teasdale and Jackson, "Signal-mediated sorting of membrane proteins between the endoplasmic reticulum and the golgi apparatus," *Annu Rev Cell Dev. Biol.*, 12:27-54, 1996.
Varkaris et al., "Src signaling pathways in prostate cancer," *Cancer Metastasis Rev.*, 33(2-3):595-606, 2014.
Watanabe et al., "Disruption of the ABC transporter genes PDR5, YOR1, and SNQ2, and their participation in improved fermentative activity of a sake yeast mutant showing pleiotropic drug resistance," *Journal of Bioscience and Bioengineering*, 89(6):569-576, 2000.
Yi et al., "Engineering of TEV protease variants by yeast ER sequestration screening (YESS) of combinatorial libraries," *PNAS*, 110(18):7229-7234, 2013.
Yi et al., "Yeast Endoplasmic Reticulum Sequestration Screening for the Engineering of Proteases from Libraries Expressed in Yeast," *Methods Mol Biol.*, 1319:81-93, 2015.
Extended European Search Report issued in European Application No. 18874197.9, dated Jul. 16, 2021.
Taft et al., "Rapid screen for tyrosine kinase inhibitor resistance mutations and substrate specificity," *ACS Chem. Biol.*, 14:1888-1895, 2019.

SEQUENCE LISTING

```
<160> NUMBER OF SEQ ID NOS: 27

<210> SEQ ID NO 1
<211> LENGTH: 11
<212> TYPE: PRT
<213> ORGANISM: Artificial sequence
<220> FEATURE:
<223> OTHER INFORMATION: Synthetic peptide

<400> SEQUENCE: 1

Ala Ala Ala Ala Ala Tyr Ala Ala Ala Ala Ala
1               5                   10

<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
acctctatac tttaacgtca aggag                                          25

<210> SEQ ID NO 3
<211> LENGTH: 18
<212> TYPE: PRT
<213> ORGANISM: Artificial sequence
<220> FEATURE:
<223> OTHER INFORMATION: Synthetic peptide

<400> SEQUENCE: 3

Met Gln Leu Leu Arg Cys Phe Ser Ile Phe Ser Val Ile Ala Ser Val
1               5                   10                  15

Leu Ala

<210> SEQ ID NO 4
<211> LENGTH: 6
<212> TYPE: PRT
```

```
<213> ORGANISM: Artificial sequence
<220> FEATURE:
<223> OTHER INFORMATION: Synthetic peptide

<400> SEQUENCE: 4

Phe Glu His Asp Glu Leu
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Lys Asp Glu Leu
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

His Asp Glu Leu
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Arg Asp Glu Leu
1

<210> SEQ ID NO 8

<400> SEQUENCE: 8

000

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Asp Tyr Lys Asp Asp Asp Asp Lys
1               5

<210> SEQ ID NO 10

<400> SEQUENCE: 10

000

<210> SEQ ID NO 11
<211> LENGTH: 6
<212> TYPE: PRT
```

```
<213> ORGANISM: Artificial sequence
<220> FEATURE:
<223> OTHER INFORMATION: Synthetic peptide

<400> SEQUENCE: 11

His His His His His His
1               5

<210> SEQ ID NO 12
<211> LENGTH: 17
<212> TYPE: PRT
<213> ORGANISM: Artificial sequence
<220> FEATURE:
<223> OTHER INFORMATION: Synthetic peptide

<400> SEQUENCE: 12

Gln Leu Leu Arg Cys Phe Ser Ile Phe Ser Val Ile Ala Ser Val Leu
1               5                   10                  15

Ala

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16
<211> LENGTH: 4
<212> TYPE: PRT
<213> ORGANISM: Artificial sequence
<220> FEATURE:
<223> OTHER INFORMATION: Synthetic peptide

<400> SEQUENCE: 16

Lys Glu Glu Leu
1

<210> SEQ ID NO 17
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 17

Lys Lys Xaa Xaa
1

<210> SEQ ID NO 18
<211> LENGTH: 10
<212> TYPE: PRT
```

```
<213> ORGANISM: Artificial sequence
<220> FEATURE:
<223> OTHER INFORMATION: Synthetic peptide

<400> SEQUENCE: 18

Val Glu Lys Pro Phe Ala Ile Ala Lys Glu
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

<400> SEQUENCE: 19

Glu Gln Lys Leu Ile Ser Glu Glu Asp Leu
1               5                   10

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Tyr Pro Tyr Asp Val Pro Asp Tyr Ala
1               5

<210> SEQ ID NO 21
<211> LENGTH: 11
<212> TYPE: PRT
<213> ORGANISM: Artificial sequence
<220> FEATURE:
<223> OTHER INFORMATION: Synthetic peptide

<400> SEQUENCE: 21

Tyr Thr Asp Ile Glu Met Asn Arg Leu Gly Lys
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthetic peptide

<400> SEQUENCE: 22

Gln Pro Glu Leu Ala Pro Glu Asp Pro Glu Asp
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic peptide

<400> SEQUENCE: 23

Gly Lys Pro Ile Pro Asn Pro Leu Leu Gly Leu Asp Ser Thr
1               5                   10

<210> SEQ ID NO 24
<211> LENGTH: 38
<212> TYPE: DNA
<213> ORGANISM: Artificial sequence
```

```
<220> FEATURE:
<223> OTHER INFORMATION: Synthetic primer

<400> SEQUENCE: 24
ggtaacggaa cgaaaaatag aaaaggatat tacatggg                                38

<210> SEQ ID NO 25
<211> LENGTH: 18
<212> TYPE: PRT
<213> ORGANISM: Artificial sequence
<220> FEATURE:
<223> OTHER INFORMATION: Synthetic peptide

<400> SEQUENCE: 25

Glu Arg Asp Ile Asn Ser Leu Tyr Asp Val Ser Arg Met Tyr Val Asp
1               5                   10                  15

Pro Ser

<210> SEQ ID NO 26
<211> LENGTH: 28
<212> TYPE: DNA
<213> ORGANISM: Artificial sequence
<220> FEATURE:
<223> OTHER INFORMATION: Synthetic primer

<400> SEQUENCE: 26
attaacggaa gcttcggatt agaagccg                                           28

<210> SEQ ID NO 27
<211> LENGTH: 37
<212> TYPE: DNA
<213> ORGANISM: Artificial sequence
<220> FEATURE:
<223> OTHER INFORMATION: Synthetic primer

<400> SEQUENCE: 27
gtgttactac tcgttattat tgcgtatttt gtgatgc                                 37
```

METHODS FOR PREDICTING KINASE INHIBITOR RESISTANCE

This application claims the benefit of U.S. Provisional Patent Application No. 62/580,556, filed Nov. 2, 2017, the entirety of which is incorporated herein by reference.

BACKGROUND OF THE INVENTION

1. Field of the Invention

The present invention relates generally to the field of molecular biology and medicine. More particularly, it concerns methods for assessing kinase inhibitors for the emergence of resistance mutations.

2. Description of Related Art

Protein kinase inhibitors, including tyrosine kinase inhibitors, have emerged as important therapeutic agents that may be used to treat a variety of diseases, such as various cancers. However, development of resistance mutations in clinical populations that are administered the kinase inhibitor presents a significant clinical challenge.

Current methods for developing new protein kinase inhibitors are generally limited in their ability to predict the emergence of resistance to the kinase inhibitor. Thus, while a kinase inhibitor may yield clinical benefits for the treatment of a disease, such as a cancer, these benefits may be quickly diminished or precluded if the cancer develops a mutation that allows the protein kinase to continue to function in the presence of the kinase inhibitor. Instances of the emergence of resistance to kinase inhibitors have been reported and are understood to be a major clinical problem (e.g., Levy et al., 2016). Clearly there is a need for both improved methods for predicting the emergence of resistance to a kinase inhibitor, as well as methods for identifying kinase inhibitors that are less likely to result in resistant populations in vivo.

SUMMARY OF THE INVENTION

The present invention overcomes limitations in the prior art by providing new methodologies to test for the possible emergence of resistance to kinase inhibitors. In some aspects, YESS methodologies are used to evolve kinases in the presence of a kinase inhibitor or test compound, and any mutant kinases that allow for continued kinase activity in the presence of the kinase inhibitor are subsequently sequenced. In this way, it may be possible to evaluate the likelihood of the emergence of resistance in clinical populations in vivo. For example, in some embodiments, the emergence of mutant kinases that include only one point mutation that allows for resistance to a kinase inhibitor indicates a significant risk for the emergence of resistance to the kinase inhibitor in clinical populations in vivo. In contrast, if two, three, or more point mutations are required in a mutant kinase to allow it to function in the presence of a kinase inhibitor, then the risk of emergence of resistance against the kinase inhibitor may be reduced. In some embodiments, methods of the present invention may be used to predict the risk of resistance to a test compound (e.g., a kinase inhibitor) prior to administration of the test compound to patients to treat a disease (e.g., cancer). In some embodiments, a library of mutant kinases is generated using low-frequency mutations or PCR errors, resulting in a library of kinases containing each of all of the possible single point mutations in the kinase, and this library of kinases may be tested for resistance to a kinase inhibitor. In some embodiments, the methods can be used to compare the risk of resistance to a first kinase inhibitor (e.g., a test compound) to a second kinase inhibitor (e.g., a clinically approved kinase inhibitor). As shown in the below examples, these approaches were used to identify mutations in kinases that provide resistance against clinically approved kinase inhibitors, and several of the identified resistance mutations have also been observed in clinical patient populations in vivo.

In some embodiments, sequential exposure to a first kinase inhibitor followed by exposure to a second kinase inhibitor can be assessed using the methods disclosed herein. Thus, in some embodiments, one may assess which ordering of subsequent administration of different kinases may yield the most clinical benefit (e.g., which kinase inhibitor should be administered first, second, and so on in order to try to minimize the chances of development of kinase resistance in the patient). For example, in some embodiments, one may perform a selection using methods disclosed herein to produce a library of mutant kinases that are resistant to a first kinase inhibitor; subsequently, one may take the library of kinase mutants and screen those mutant kinases against a second kinase inhibitor (e.g., to see if any of the mutant kinases display or can easily develop resistance to the second kinase inhibitor). This sequential screening can mimic what happens in the clinic when a patient is treated with one kinase inhibitor drug, becomes resistant to the drug, and then is treated with a different kinase inhibitor drug. Further, this approach may allow one to determine which sequential administration may yield the best therapeutic results. For example, if several or many of the mutant kinases resistant to a first kinase inhibitor are often also resistant to a second kinase inhibitor, but the few or none of the mutant kinases resistant to the second kinase inhibitor are resistant to the first kinase inhibitor, then it may be clinically advantageous to administer the second kinase inhibitor before the first kinase inhibitor. When two different kinase inhibitors are sequentially tested for emergence of resistance, the order of the kinase inhibitors may be varied. Similarly, this approach may be used to test for the emergence of resistance to a kinase inhibitor based on the sequential screening of three or more kinase inhibitors.

An aspect of the present invention relates to a method of generating a mutant kinase, comprising: (a) expressing in each of a plurality of eukaryotic cells: (i) a first fusion protein comprising an ER targeting sequence, a kinase, and an ER retention sequence; and (ii) a vector encoding a second fusion protein comprising: an endoplasmic reticulum (ER) targeting sequence, a surface expression sequence, a first peptide sequence, and a endoplasmic reticulum (ER) retention sequence; wherein the eukaryotic cells are exposed to a kinase inhibitor during said expression; and (b) separating or purifying said eukaryotic cells based on the presence or absence of phosphorylation of at least one amino acid of the first peptide on the surface of the eukaryotic cells. In some embodiments, the method further comprises (c) wherein if at least some eukaryotic cells have said presence of phosphorylation of at least one amino acid, then the method further comprises sequencing kinases expressed by the eukaryotic cells having said presence of phosphorylation of at least one amino acid of the first peptide. The kinase may be at least partially randomized. In some embodiments, the kinase is resistant to inhibition by the kinase inhibitor. In some embodiments, the kinase is a tyrosine kinase or a Src kinase. The eukaryotic cell may be a yeast such as, e.g., a Kex2 (−/−) knockout yeast. In some embodiments, the yeast has one, two, or all of the SNQ2, YOR1, and/or PDQ5 genes knocked out. SNQ2, YOR1, and PDQ5 can function as small molecule transporters, and by knocking out one or more of these genes (e.g., in a yeast) it may be possible to reduce the export of a kinase inhibitor from the cell. In some embodiments, the enzyme is a kinase, and wherein the vector encodes a second fusion protein comprises in an N- to C-direction: an endoplasmic reticulum (ER) targeting sequence, a surface expression sequence, the first peptide sequence, and an endoplasmic reticulum (ER) retention sequence. The sequencing may comprise next-generation sequencing. The next-generation sequencing may comprise or consist of single-molecule real-time sequencing, an ion semiconductor method, a pyrosequencing method, a sequencing by synthesis method, or a sequencing by ligation method. The method may further comprise analyzing data from said sequencing with a computer. In some embodiments, the endoplasmic reticulum (ER) targeting sequence encoded in the vector is comprised in said surface expression sequence in the vector. In some embodiments, the surface expression sequence is Aga2. The method may further comprise repeating steps (a) and (b). The separating may comprise or consist of fluorescence-activated cell sorting (FACS). The method may comprise repeated FACS separation and culture of the eukaryotic cells. In some embodiments, the enzyme is a kinase and wherein step (b) comprises FACS separation of cells via an antibody that selectively binds a phosphorylated amino acid. The phosphorylated amino acid may be a tyrosine. In some embodiments, the kinase is a human kinase (e.g., a tyrosine kinase). In some embodiments, the tyrosine kinase is a receptor tyrosine kinase or a non-receptor tyrosine kinase. The non-receptor tyrosine kinase may be a Src kinase (e.g., c-SRC, YES1, Fyn, Fgr, Lck, HCK, BTK, Blk, Lyn, or Frk). In some embodiments, the kinase is ABL kinase, c-SRC, Lyn, or BTK. In some embodiments, a first promoter controls expression of the first fusion protein, wherein the first promoter is expressable in yeast. The first promoter may be Gal1, Gal10, or Gal4-BS2-pleum. In some embodiments, the endoplasmic reticulum (ER) targeting sequence is MQLLRCFSIFSVIASVLA (SEQ ID NO:3). In some embodiments, the endoplasmic reticulum (ER) retention sequence is FEHDEL (SEQ ID NO:4), KDEL (SEQ ID NO:5), HDEL (SEQ ID NO:6), or RDEL (SEQ ID NO:7). The purifying or separating may comprise separating the cells based on the presence or absence of a first antibody that selectively binds a phosphorylated amino acid (e.g., a tyrosine). The antibody may be labeled with a fluorophore. The purifying or separating may comprise or consist of fluorescence activated cell sorting (FACS). The method may further comprise an in vitro method for evaluating the risk of resistance to the kinase inhibitor in vivo.

In some embodiments, multiple resistant mutant kinases are generated and sequenced. The multiple mutant kinases are generated by error prone PCR (e.g., low-frequency error prone PCR). The multiple mutant kinases may be generated by site directed mutagenesis. In some embodiments, the multiple mutant kinases are obtained from a library. In some embodiments, at least 1, 2, 3, 4, 5, 6, 7, 8, 9, or 10 single mutations are observed to provide resistance to the kinase inhibitor. In some embodiments, at least 1, 2, 3, 4, 5, 6, 7, 8, 9, or 10 double mutations are observed to provide resistance to the kinase inhibitor. In some embodiments, at least one of the multiple resistant kinases comprises a mutation that has been observed in a subject that is resistant to the kinase inhibitor in vivo. The mutations in the resistant mutant kinases may be compared to a listing of mutations that can result in resistance to a second kinase inhibitor such as, e.g., a kinase inhibitor has been approved for clinical use in vivo. In some embodiments, the listing is generated using a method of the present disclosure or as described above. In some embodiments, the listing is obtained by sequencing kinases obtained from patients resistant to the second kinase inhibitor. In some embodiments, the eukaryotic cell is a yeast, wherein the yeast has one or more transporter genes knocked out. For example, in some embodiments, the yeast is a null mutant for 1, 2, or all of SNQ2, YOR1, and/or PDR5.

In some embodiments, the YESS method for measuring the activity of a kinase in in a eukaryotic cell such as a yeast, comprises: (a) expressing in each of a plurality of eukaryotic cells: (i) a first fusion protein comprising an ER targeting sequence, a kinase, and an ER retention sequence; and (ii) the vector encodes a second fusion protein comprising: an endoplasmic reticulum (ER) targeting sequence, a surface expression sequence, a first peptide sequence, and a endoplasmic reticulum (ER) retention sequence; wherein the eukaryotic cells are exposed to a kinase inhibitor during said expression; (b) separating or purifying said eukaryotic cells based on the presence or absence of phosphorylation of at least one amino acid of the first peptide on the surface of the eukaryotic cells; and (c) wherein if at least some eukaryotic cells have said presence of phosphorylation of at least one amino acid, then the method preferably further comprises sequencing kinases expressed by the eukaryotic cells having said presence of phosphorylation of at least one amino acid of the first peptide. In some embodiments, the vector encodes the second fusion protein in an N- to C-direction: an endoplasmic reticulum (ER) targeting sequence, a surface expression sequence, the first peptide sequence, and an endoplasmic reticulum (ER) retention sequence. In some embodiments, the vector encodes the second fusion protein in an N- to C-direction: an endoplasmic reticulum (ER) targeting sequence, the first peptide sequence, a surface expression sequence, and a endoplasmic reticulum (ER) retention sequence. In some embodiments, it may be possible to exclude the surface expression sequence from the second vector, if desired. In some preferred embodiments, the eukaryotic cell is a yeast cell (e.g., a Kex2 knockout yeast cell).

In some embodiments, said sequencing comprises next-generation sequencing. In some preferred embodiments, the next-generation sequencing system is capable of longer reads that allow one to identify multiple mutations in a single kinase, e.g., a Pacific Biosciences sequencing system. The next-generation sequencing may comprise single-molecule real-time sequencing, an ion semiconductor method, a pyro sequencing method, a sequencing by synthesis method, or a sequencing by ligation method. The method may further comprise analyzing data from said sequencing with a computer. For example, said analyzing may comprises excluding sequences comprising a stop codon. In some embodiments, the endoplasmic reticulum (ER) targeting sequence encoded in the vector is comprised in the surface expression sequence in the vector. The surface expression sequence may be Aga2. In some embodiments, step (b) comprises repeated separations or multiple rounds of separation. In some embodiments, step (b) comprises multiple rounds of FACS separation and expansion or culture of the eukaryotic cells. The method may further comprise repeating steps (a) and (b). In some embodiments, the method comprises repeated FACS separation and culture of the eukaryotic cells. In some embodiments, the first peptide may be less than 20 amino acids in length, less than 10 amino acids in length, or 4, 5, 6, 7, or 8 amino acids in length. The first peptide may be comprised in a protein, wherein the protein is encoded by the vector; however, in some preferred embodiments, the first peptide is not comprised in a protein. In some embodiments, the first peptide comprises one or more tyrosine residues that is flanked upstream and downstream by multiple alanine residues. In some embodiments, said separating comprises fluorescence-activated cell sorting (FACS). In some embodiments, step (b) comprises FACS separation of cells via an antibody that selectively binds a phosphorylated amino acid (e.g., a phosphorylated tyrosine). In some embodiments, the kinase is a human kinase, such as a tyrosine kinase or a Src kinase (e.g., c-SRC, YES1, Fyn, Fgr, Lck, HCK, Blk, Lyn, or Frk). In some embodiments, the kinase is a wild-type kinase. In some embodiments, the kinase is mutated relative to wild-type. The kinase may be a mutated kinase, e.g., comprising 1, 2, 3, 4, 5, 6, or more substitution mutations, additions, or deletions as compared to the native or wild-type kinase but otherwise shares complete amino acid sequence with the native or wild-type kinase. In some embodiments, a first promoter controls expression of the first fusion protein, wherein the first promoter is expressible in yeast. The first promoter may be Gal1, Gal10, or Gal4-BS2-pleum. The endoplasmic reticulum (ER) targeting sequence may be MQLLRCFSIFSVIASVLA (SEQ ID NO:3). The endoplasmic reticulum (ER) retention sequence may be FEHDEL (SEQ ID NO:4), KDEL (SEQ ID NO:5), HDEL (SEQ ID NO:6), or RDEL (SEQ ID NO:7). YESS methodologies are that may be utilized in various embodiments are described, e.g., in U.S. Pat. Nos. 8,945,855, 9,546,359, PCT/US15/55494, Li et al. (2017), and Yi et al. (2013), which are incorporated herein by reference in their entirety.

In some embodiments, the yeast has one or more transporter gene knocked out. For example, the yeast may have 1, 2, or all of the following genes knocked out: SNQ2, YOR1, and PDR5; in some embodiments, the yeast is a triple-knockout where all of SNQ2, YOR1, and PDR5 have been knocked out. Since transporters can export some drugs from yeast (e.g., Watanabe et al., 2000; Kolaczkowska et al., 2008), by knocking out the transporter in yeast it is anticipated that this approach may be used to increase interactions between a drug or test compound with one or more kinases in the cell. In some embodiments, it is anticipated that homologous transporter genes may be similarly knocked out in other eukaryotic cells, if desired.

The term "antibody" is used herein in the broadest sense and specifically encompasses at least monoclonal antibodies, polyclonal antibodies, multi-specific antibodies (e.g., bispecific antibodies), naturally polyspecific antibodies, chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes.

"Antibody fragments" comprise a portion of an intact antibody, for example, one or more portions of the antigen-binding region thereof. Examples of antibody fragments include Fab, Fab', F(ab')2, and Fv fragments, diabodies, linear antibodies, single-chain antibodies, and multi-specific antibodies formed from intact antibodies and antibody fragments.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody.

As used herein, the term "complementary nucleotide sequence" refers to a sequence of nucleotides in a single-stranded molecule of DNA or RNA that is sufficiently complementary to that on another single strand to specifically hybridize to it with consequent hydrogen bonding.

An "expression vector" is intended to be any nucleotide molecule used to transport genetic information.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
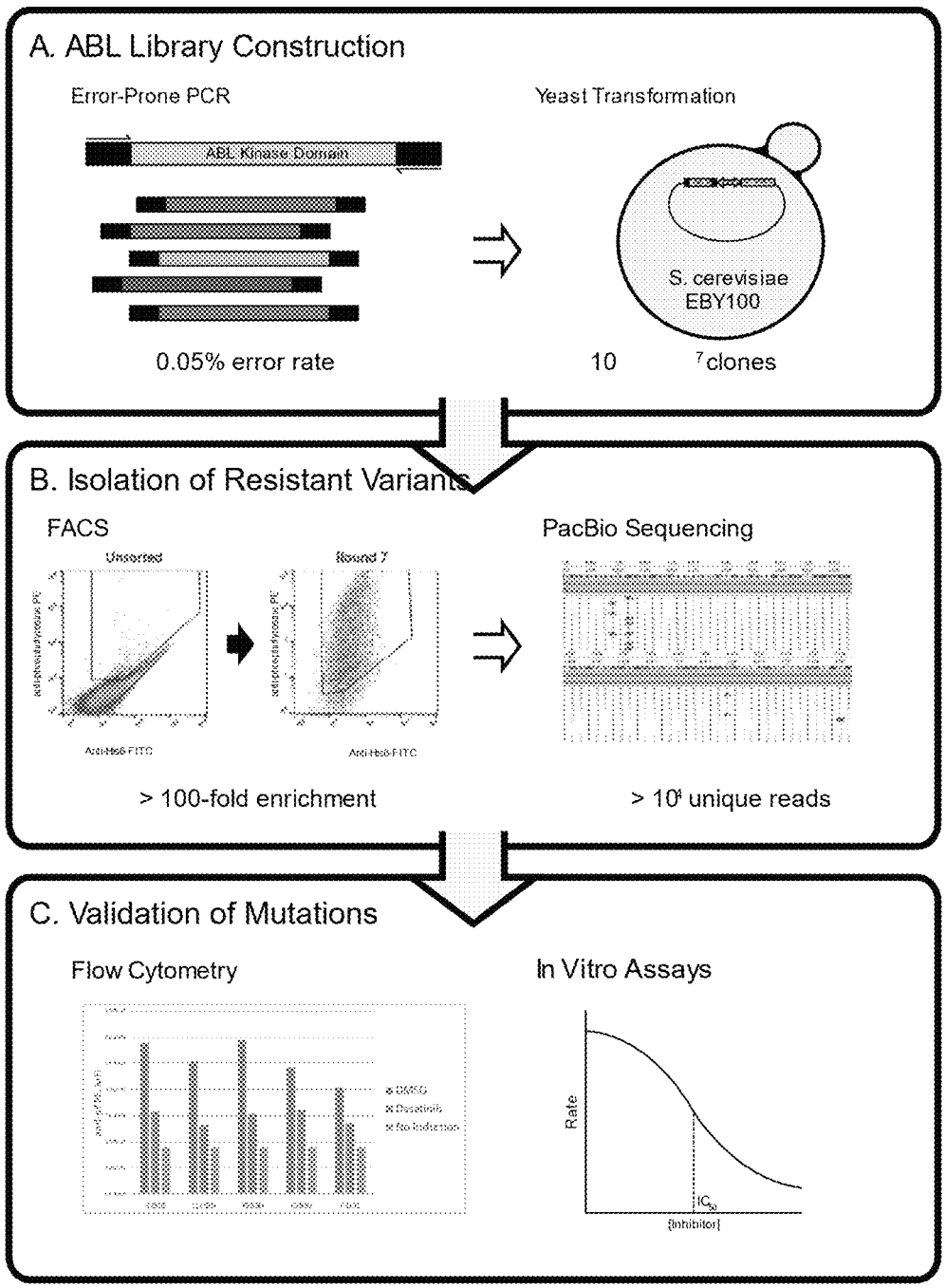
FIG. 1: Schematic of an example of library construction, expression and separation of mutant or resistant kinases, and sequencing of mutant or resistant kinases.

The present invention overcomes limitations in the prior art by providing, in some aspects, methods for assessing kinase inhibitors for the emergence of resistance mutations. In some embodiments, yeast endoplasmic reticulum sequestration sequencing (YESS) is used to evolve kinases that exhibit resistance to a test compound or kinase inhibitor (e.g., a tyrosine kinase inhibitor, a Src kinase inhibitor). In some aspects, by evolving mutant kinases in the presence of a kinase inhibitor, mutant kinases that display resistance to inhibition by the kinase inhibitor may be identified. For example, as shown in the below examples these methods have been utilized to identify resistance mutations in vitro that have also been observed in vivo. In some aspects, the likelihood of the emergence of resistance mutations in patient populations that might receive the kinase inhibitor (e.g., cancer patients, etc.) can be assessed by the results of the identified resistance mutations. For example, for a particular kinase inhibitor, if multiple instances of a single point mutation are observed to confer resistance to the kinase inhibitor, then a significant risk for the development of resistance against the kinase inhibitor may be expected when the kinase inhibitor is administered to patient populations in the clinic over a period of time. Alternately, if only multiple point mutations in a kinase (e.g., two, three, or more substitution mutations) are observed to confer resistance to the kinase inhibitor, then these results can indicate a decreased risk for the development of resistance the kinase when administered clinically to patient populations. In some aspects, methods described herein may be utilized, e.g., to assist in the process of selecting kinase inhibitors that may warrant further clinical testing or usage. Wild-type or mutant kinases may be screened for resistance against a kinase inhibitor using methods provided herein. In some embodiments, the subsequent screening of a library of kinases with different kinase inhibitors may be performed, e.g., to determine which order kinase inhibitors could be administered to a patient in order to minimize the emergence of resistance and/or increase the therapeutic response.

I. YESS SCREENING METHODS

In some aspects, methods of screening a test compound or kinase inhibitor for resistance mutations may involve evolving or expressing kinases in the presence of a kinase inhibitor using yeast endoplasmic reticulum (ER) sequestration screening (YESS) methods. YESS methodologies are described, e.g., in U.S. Pat. Nos. 8,945,855, 9,546,359, PCT/US15/55494, and Li et al. (2017) and Yi et al. (2013), which are incorporated herein by reference in their entirety. In some embodiments, 1, 2, 3, 4, or more rounds of YESS screening may be performed to evolve a kinase in the presence of a test compound or a kinase inhibitor, and then the resulting mutant kinases that are resistant to inhibition by the test compound or kinase inhibitor may be sequenced (e.g., using next-generation DNA sequencing). In some embodiments, next-generation DNA sequencing methods such as Oxford Nanopore Technologies (Nanopore) or Pacific Biosciences (PacBio®) may be used in order to obtain longer reads in order to allow for identification of mutations over a wider portion of the kinase; for example, average lengths of 700 bp, 10 kb and 15 kb and maximum lengths of 1 kb, 10 kb and 15 kb using these methods (Escalona et al., 2016).

YESS methods used in various aspects of the present invention generally involve expression of kinases in yeast, or other eukaryotic or mammalian cells, for high-throughput screening. YESS may be used to identify evolved protein kinases that are resistant to inhibition by a kinase inhibitor or a test compound, and yeast cells expressing kinases that are resistant to a kinase inhibitor or test compound can be separated, e.g., using fluorescence activated cell sorting (FACS). For example, if a kinase can phosphorylate a target sequence expressed on the surface of yeast, then this phosphorylated amino acid may be bound by an antibody that selectively binds to the phosphorylated sequence and is tagged with a fluorescent label, and then the yeast may be separated based on fluorescence of the bound antibody using FACS. YESS may involve the targeted interaction of the protein kinase variant with a target sequence in the yeast endoplasmic reticulum (ER), in the presence of a kinase inhibitor. Following reaction with the kinase in the ER, substrate phosphorylation products are preferably directed to display on the yeast surface and detected with labeled antibodies. Cells that express a kinase that is resistant to the kinase inhibitor can be separated (e.g., using FACS) and sequenced. For example, antibodies that selectively bind a phosphorylated amino acid in an amino acid sequence may be used to detect phosphorylation by a wild-type or mutant kinase using these methods.

In some preferred embodiments, the YESS platform is used in combination with NextGen sequencing and a comparative sequence analysis is performed to identify mutant kinases that are resistant to inhibition of activity in the presence of a kinase inhibitor or a test compound. Nonetheless, in some embodiments, a library of kinases may include wild-type kinases and/or kinases which have been previously identified as resistant to inhibition or inhibition by kinase inhibitors. Generally, an Aga2-tagged substrate library (expressing (i) a kinase, such as a kinase with one or more randomized portions or one or more kinases that have a mutation that may lead to resistance to a kinase inhibitor, and (ii) a target sequence comprising a sequence that may be phosphorylated by the kinase) is targeted to the yeast endoplasmic reticulum (ER) and transported through the secretory pathway, where the kinase can interact with a target sequence (encoding a sequence that can be phosphorylated by the kinase in the absence of a kinase inhibitor, such as by a corresponding wild-type kinase in the absence of a kinase inhibitor) in the ER. Preferably this interaction between the kinase and the target sequence occurs in the presence of a kinase inhibitor or a test compound. After being transported outside of the cell and attached to the yeast surface, the substrate/product can be probed with fluorescently labeled antibodies for the presence or absence of phosphorylation of the target sequence. This process may be carried out in the presence or absence of a kinase inhibitor or test compound. In some preferred embodiments, the yeast cells are incubated in the presence of a kinase inhibitor or a test compound, in order to select for mutant kinases that are resistant to inhibition by the kinase inhibitor or test compound. An expression tag may also be expressed in a fusion construct with the target sequence, and the expression tag may facilitate separation of cells that express a phosphorylated target sequence. Multi-color FACS screening may then be used to isolate cells with appropriately phosphorylated substrate. This process may be repeated 1, 2, 3, 4, or more times, as desired. Then, next generation DNA sequencing (NextGen) may be used to determine the sequence of the kinases that are resistant to inhibition by the kinase inhibitor or the test compound.

In some embodiments, the yeast cleaveOme identified by this method may be used to prepare target sequences that may avoid degradation when transported via the yeast secretory pathway (Yi et al., 2017). Such embodiments may be particularly useful to address or avoid problems associated with proteolytic degradation of a recombinant protein in a yeast cell during production of the recombinant protein in yeast. In some embodiments, Kex2 knockout yeast (e.g., EBY100$^{Kex2}$) are used to express the kinase and substrate sequence. Kex2 (also known as kexin, peptidase 3.4.21.61) exists in the yeast secretory pathway (Seidah et al. 2002), and use of Kex2 knockout yeast may facilitate expression of kinases in the endoplasmic reticulum (ER), without undesired cleavage of the kinase or substrate sequence in the ER of the yeast.

Some aspects relate to detecting the kinase activity in a eukaryotic cell, such as a yeast (e.g., a Kex2 knockout yeast). A vector expressing a first fusion protein comprising a peptide sequence and cell surface expression sequence may be expressed in the cell. Then, the presence or absence of phosphorylation of an amino acid in the peptide may be detected, e.g., using FACS, based on the presence or absence of the binding of an antibody that selectively recognizes a phosphorylated amino acid. As would be appreciated by one of skill in the art, several antibodies that selectively recognize phosphorylated amino acids (e.g., phosphor-tyrosine, etc.) are commercially available. The first fusion protein may further comprise an ER targeting and ER retention sequence. A wild-type or engineered kinase (e.g., a kinase with a randomized portion, or select kinases that may be resistant to inhibition by a kinase inhibitor) may also be expressed in the cell, e.g., in the same vector as the first fusion protein or in a different vector. In some embodiments, a portion of the kinase is randomized. The kinase may further comprise an ER targeting and ER retention sequence. In this way, when the kinase and the first fusion protein each comprise an ER targeting and ER retention sequence, the kinase and first fusion protein may be brought into closer proximity in the ER and/or benefit from the improved folding environment of the ER. The yeast may be incubated in the presence of a kinase inhibitor or a test compound. In some embodiments, the activity of a kinase may be measured by expressing the kinase in eukaryotic cells with the first fusion protein, detecting the activity of the kinases expressed by the yeast cells, separating the cells that exhibit kinase activity in the presence of the kinase inhibitor or test compound, and subsequently sequencing the kinases that are resistant to inhibition (e.g., via next-generation sequencing).

Another aspect of the present invention relates to a method of measuring the activity or specificity of a kinase, comprising: (a) expressing a in a plurality of eukaryotic cells a vector encoding an endoplasmic reticulum (ER) targeting sequence and a endoplasmic reticulum (ER) retention sequence, a surface expression sequence and the first peptide sequence; (b) purifying or separating the cells based on the presence or absence of a first antibody that selectively binds a phosphorylated amino acid; (c) sequencing the first peptide sequences after step (b) to produce a dataset; and (d) subtracting or eliminating endogenous kinase activity in the eukaryotic cells from the dataset. In some aspects, the endogenous kinase activity of a cell or yeast may be determined by a method of the present invention. The cells may be yeast cells (e.g., Kex2 knockout yeast cells). The antibody may be labeled with a fluorophore. The purifying or separating may comprise or consists of fluorescence activated cell sorting (FACS).

The method may further comprise expressing a kinase in the yeast and/or randomizing one or more amino acids in the kinase. The method may comprise further characterizing the kinase. The kinase may be a human kinase such as, e.g., a tyrosine kinase or a Src kinase. The kinase may be a wild-type kinase. In some embodiments, the kinase is mutated relative to wild-type. In some embodiments, at least a portion of the kinase is randomized. In some embodiments, the method is further defined as a method of generating an engineered kinase, wherein step (b) is repeated. In some embodiments, the first endoplasmic reticulum (ER) targeting sequence and the second endoplasmic reticulum (ER) targeting sequence are MQLLRCFSIFSVIASVLA (SEQ ID NO:3). In some embodiments, the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7). The kinase may be a mutated kinase, e.g., comprising 1, 2, 3, 4, 5, 6, or more substitution mutations, additions, or deletions as compared to the native or wild-type kinase but otherwise shares complete amino acid sequence with the native or wild-type kinase. In some embodiments, a first promoter controls expression of the first fusion protein, and a second promoter controls expression of the second fusion protein. The first promoter and the second promoter are preferably expressible in yeast. In some embodiments, the first promoter is Gal1, Gal10, or Gal4-BS2-pleum. In some embodiments, the second promoter is Gal1, Gal10, or Gal4-BS2-pleum.

A variety of concentrations of the kinase inhibitor or test compound may be used to incubate yeast during the expression of the kinase and the target sequence. In some embodiments, a kinase inhibitor is used at a concentration that approximates or is similar to concentrations that would be used clinically or might be achieved in vivo. In other embodiments, concentrations of the kinase inhibitor may be used which are substantially above or below the concentrations of the kinase inhibitor that would be used clinically or that may be achieved in vivo. For example, incubating yeast that express the kinase and the target sequence with a kinase inhibitor present at concentrations higher than may be achieved in vivo may be used to identify kinase mutants that exhibit increased resistance to inhibition by the kinase inhibitor. In some embodiments, 0.1, 1, 5, 10, 15, 20, 25, 30, 40, 50 µM or more or any range derivable therein of a kinase inhibitor may be used. In some embodiments, the yeast are incubated in the presence of kinase inhibitor or test compound at a concentration that is similar to or within a range that could be used clinically or that might be achieved in vivo, and then the observed mutant kinases can be sequenced to assess the risk of the kinase inhibitor or test compound to the development of resistance, e.g., if administered clinically (e.g., to cancer patients, etc.). Kinase inhibitors that may be tested with and/or used in various aspects of the present invention include, e.g., afatinib, axitinib, bosutinib, cetuximab, cobimetinib, crizotinib, cabozantinib, dasatinib, entrectinib, erlotinib, fostamatinib, gefitinib, ibrutinib, imatinib, lapatinib, lenvatinib, mubritinib, nilotinib, pazopanib, pegaptanib, ponatinib, ruxolitinib, sorafenib, sunitinib, SU6656, vandetanib, and/or vemurafenib. In some embodiments, cells are incubated in the presence of kinase inhibitor a concentration that is similar to or essentially the same as a concentration of the kinase inhibitor that may be achieved in vivo, to identify resistant mutant kinases.

In some embodiments, the methods described herein may be used to evaluate the risk of emergence of resistance to a test compound or a first kinase inhibitor, and this data may be compared with data obtained using the methods on a second kinase inhibitor or an approved kinase inhibitor. In some embodiments, YESS sequencing may be used to identify mutations that are capable of allowing a kinase to function in the presence of a test kinase inhibitor, and by comparing the mutations that are required to impart resistance to the test compound to resistance mutations observed for a clinically approved kinase inhibitor, one may be able to predict if the development of resistance in vivo is more likely or less likely for the test kinase inhibitor, as compared to the clinically approved kinase inhibitor. For example, if few or no single mutations, and only some double or triple mutations are observed to provide resistance to a kinase against a test kinase inhibitor, then the chances for the development of resistance in vivo would be less than for a second kinase inhibitor (e.g., an approved kinase inhibitor), where the second kinase inhibitor has more or many single mutations that can result in resistance. Similarly, 2, 3, 4, 5, 6, 7, 8, 9, 10, 11, 12, or more approved kinase inhibitors may be tested using the methods described herein to allow for the ranking of the kinase inhibitors according to relative risk for the development of resistance in vivo. For example, as shown in the below examples, multiple single mutations were observed to provide resistance against dasatinib, and fewer single mutations and more double mutants were observed to provide resistance against ponatinib; thus, the risk for the emergence of resistance in vivo is greater for dasatinib than for ponatinib.

II. KINASE INHIBITORS

Protein kinases are well known in the art, and aberrant or increased activity of these enzymes have been associated with a variety of diseases, including cancers. Protein kinases typically add a phosphate ($PO_4$) group to an amino acid in a protein, such as a tyrosine in the case of tyrosine kinases. Kinase inhibitors, also called protein kinase inhibitors, inhibit the activity of the protein kinase. In some embodiments, the kinase inhibitor inhibits a tyrosine kinase. In some embodiments, a kinase inhibitor may be tested via the methods disclosed herein in order to assess the risk or resistance prior to administration to human subjects.

In some embodiments, kinases can be evolved (e.g., using YESS) in the presence of a known or approved protein kinase inhibitor, to identify resistance mutations. The resulting mutants that are observed from evolution of kinases in the presence of the known or approved kinase inhibitor may be useful, e.g., for a medical professional when deciding which kinase inhibitor to prescribe to a patient. In some embodiments, kinases are evolved in the presence of a test compound or test kinase inhibitor (e.g., that is not yet clinically approved), and the resulting resistance mutations may be compared to the resistance mutations observed for a known or approved kinase inhibitor; in this way, the methods may be used to predict if the risk for the development of resistance mutation(s) is greater than or less than the risk associated with the known or approved kinase inhibitor.

In some embodiments, kinases can be evolved (e.g., using YESS) in the presence of two protein kinase inhibitors. In these embodiments, particular combinations of kinase inhibitors may be identified that may be particularly useful for decreasing the chances of emergence of resistance mutations in clinical populations. Thus, these approaches may be used to identify combinations of kinase inhibitors that may be co-administered to a subject to reduce the chances of the emergence of A variety of protein kinase inhibitors are known and may be used in various embodiments of the present invention. For example, the protein kinase inhibitor may be a tyrosine kinase inhibitor such as, e.g., gefitinib, imatinib, dasatinib, nilotinib, bosutinib, or ponatinib. In some embodiments, the kinase inhibitor is afatinib, axitinib, bosutinib, cetuximab, cobimetinib, crizotinib, cabozantinib, dasatinib, entrectinib, erlotinib, fostamatinib, gefitinib, ibrutinib, imatinib, lapatinib, lenvatinib, mubritinib, nilotinib, pazopanib, pegaptanib, ponatinib, ruxolitinib, sorafenib, sunitinib, SU6656, vandetanib, and/or vemurafenib. In some embodiments, the protein kinase inhibitor has not been clinically approved or is a test compound (e.g., a small molecule, an antibody, or an antibody fragment, etc.). In some embodiments, a test compound may be tested to identify mutant kinase(s) that are resistant to inhibition by the test compound, and these results may optionally be compared to results obtained for mutant kinases that are resistant to inhibition by an approved kinase inhibitor; in this way, it may be possible to evaluate whether or not the test compound may be more or less likely to result in resistant patient populations in vivo, as compared to the approved kinase inhibitor.

In some embodiments, the kinase inhibitor or test compound may be useful for the treatment of a disease such as, e.g., a cancer. For example, in some embodiments, the cancer is a non-small cell lung cancer (NSCLC), a lung cancer, chronic myeloid leukemia (CML), gastrointestinal stromal tumors (GIST), renal cell carcinoma, a melanoma, a breast cancer, a thyroid cancer, a renal cancer, a soft tissue sarcoma, a leukemia, chronic lymphocytic leukemia (CLL), small lymphocytic lymphoma (SLL), a B-cell malignancy, a pancreatic cancer, colorectal cancer, a bone cancer, a gastrointestinal cancer, a brain cancer, a thyroid cancer, or other cancer. The cancer may be metastatic or non-metastatic. In some embodiments, the disease is inflammation or an autoimmune disease.

III. KINASES

A variety of kinases may be expressed and tested in various embodiments of the present invention. For example, in some embodiments, the kinase is a tyrosine kinase. Tyrosine kinases can catalytically covalently attach a phosphate group to the amino acid tyrosine on a protein. Tyrosine kinases are well known to affect signal transduction involved in cellular activities such as cell division, and overexpression of tyrosine kinases in a cell can result in or promote the emergence of cancers, including non-small cell lung cancer, chronic myeloid leukemia, and gastrointestinal stromal tumors.

In some embodiments, the tyrosine kinase is a receptor tyrosine kinase or a non-receptor tyrosine kinase. For example, in some embodiments, the tyrosine kinase is a receptor tyrosine kinase such as a RTK class I (EGF receptor family) (ErbB family), RTK class II (Insulin receptor family), RTK class III (PDGF receptor family), RTK class IV (VEGF receptors family), RTK class V (FGF receptor family), RTK class VI (CCK receptor family), RTK class VII (NGF receptor family), RTK class VIII (HGF receptor family), RTK class IX (Eph receptor family), RTK class X (AXL receptor family), RTK class XI (TIE receptor family), RTK class XII (RYK receptor family), RTK class XIII (DDR receptor family), RTK class XIV (RET receptor family), RTK class XV (ROS receptor family), RTK class XVI (LTK receptor family), RTK class XVII (ROR receptor family), RTK class XVIII (MuSK receptor family), RTK class XIX (LMR receptor), or a RTK class XX tyrosine kinase. In some embodiments, in tyrosine kinase is not a receptor tyrosine kinase.

In some embodiments, the tyrosine kinase is a cytoplasmic or non-receptor tyrosine kinase, such as a Src kinase or an Abl kinase. In some embodiments, the tyrosine kinase is a Src kinase such as c-Src, Yes, Fyn, Fgr, Yrk, Lyn, Blk, Hck, or Lck. In some embodiments, the kinase is Bruton's tyrosine kinase (BTK). A variety of tyrosine kinases are known and may be used in various embodiments (e.g., Espada et al., 2017; Varkaris et al., 2014.).

IV. NUCLEIC ACID CONSTRUCTS

Certain aspects of the present invention involve nucleic acids that encode an enzyme (e.g., kinase) that can modify a genetically encoded substrate and/or an amino acid substrate. The enzyme (e.g., kinase) and the substrate may be expressed as a fusion protein with one or more additional sequences, such as an ER targeting sequence, an ER retention sequence, a cell-surface sequence, and/or one or more immunotag sequences. In some embodiments, a single nucleic acid may be used to express both a kinase and an amino acid substrate in a cell. It is generally anticipated that, although expressing both a kinase and an amino acid substrate from a single vector or construct may effectively allow for interactions between the kinase and amino acid substrate in a cell, in some embodiments the kinase and amino acid substrate may be encoded by two different or separate nucleic acids or vectors, and the two nucleic acids may be expressed in a cell, such as a yeast cell.

In some embodiments, the following construct may be generated and used. Under the control of the GAL10 promoter and after the Aga2 gene used for yeast surface display, a five-part cassette may be cloned that includes; (1) a first epitope tag sequence (e.g., a FLAG tag, DYKDDDDK, SEQ ID NO:9); (2) an amino acid sequence that can be phosphorylated by the wild-type kinase; (4) an second epitope tag (e.g., 6× His tag, HHHHHH, SEQ ID NO:11); and (5) an ER retention signal peptide (e.g., FEHDEL, SEQ ID NO:4). Under the control of the GAL1 promoter, a kinase library (e.g., a library of mutant kinases, a library of kinases comprising one or more random mutations, a library of kinases comprising mutant kinases resistant to inhibition by a kinase inhibitor) may be cloned along with a designed N-terminal ER targeting signal peptide (QLLRCFSIFSVIASVLA, SEQ ID NO:12) and with or without a C-terminal ER retention signal peptide. If desired, the first epitope tag sequence and/or the second epitope tag sequence may be excluded from the construct.

It is anticipated that a variety of target sequences may be used that may be phosphorylated by a kinase. Examples of target sequences that may be used in various embodiments of the present invention include, but are not limited to: AAAAAYAAAAA (SEQ ID NO:1), e.g., in embodiments using Abl kinase.

Endoplasmic Reticulum (ER) Targeting Sequences

The construct may comprise 1, 2, or more sequences for targeting an amino acid sequence (e.g., comprising a kinase or a substrate sequence) to the endoplasmic reticulum (ER). In some embodiments, the HDEL (SEQ ID NO:6) system may be used as described in Monnat et al. (2000), which is incorporated by reference herein in its entirety. In some embodiments, the ER targeting signal peptide (QLLRCFSIFSVIASVLA, SEQ ID NO:12) is used. The ER targeting signal peptide may be at or near the N-terminal portion such that an amino acid comprising a kinase or substrate sequence can be targeted to the ER.

Without wishing to be bound by any theory, the ER targeting sequence may bind a ribosome and allow for the amino acid to be transported into the ER. Generally, an ER targeting sequence may promote entry of an amino acid sequence, peptide, or protein, by promoting entry of the protein into the ER through the translocon, e.g., via a protein-conducting channel formed by a conserved, heterotrimeric membrane-protein complex referred to as the Sec61 or SecY complex. In some embodiments, a sequence disclosed as an ER targeting sequence of Rapoport (2007), Hedge and Keenan (2011), or Park and Rapoport (2012) may be used with the present invention. In some embodiments, an N-terminal targeting sequence for promoting entry into the endoplasmic reticulum may be identified via the Predotar (Prediction of Organelle Targeting sequences) method disclosed in Small et al. (2004).

Endoplasmic Reticulum (ER) Retention Sequences

Once in the ER, in certain embodiments, it may be preferable to include an ER retention sequence or peptide in order to allow or promote an amino acid (e.g., comprising a kinase or a substrate sequence) to remain in the interior of the ER.

In some embodiments, the ER retention signal peptide is FEHDEL (SEQ ID NO:4). The HDEL (SEQ ID NO:6) system may be used as described in Monnat et al. (2000). In some embodiments, a protein chimera may be generated that contains a C-terminal tetrapeptide sequences of (-KDEL (SEQ ID NO:5), -HDEL (SEQ ID NO:6), or -RDEL (SEQ ID NO:7)) to promote retention in the ER. If only a partial retention in the ER is desired, a protein chimera may be generated that contains C-terminal sequence (-KEEL, SEQ ID NO:16). In some embodiments where it is desirable to use a mammalian cell line for expression of constructs, it may be useful to use the mammalian (-KDEL, SEQ ID NO:5) sequence in a fusion protein with a kinase and/or a substrate. The particular ER retention sequence used may be chosen based on the amount of retention in the ER produced in a particular eukaryotic cell type. In some embodiments, an upstream sequence beyond the C-terminal tetrapeptide may be included that can influence or may be part of the structure of reticuloplasmin retention signals. In various aspects, a sequence may be included in a chimeric kinase or in a chimeric substrate that promotes retention of the protein or peptide in the ER by affecting sorting of exported protein, retention of residents, and/or retrieval of escapees.

HDEL (SEQ ID NO:6) sequences are further described in Denecke et al. (1992). In some embodiments, an ER targeting sequence or ER retention sequence of Copic et al. (2009) may be used. In some embodiments, an ER-targeting sequence, such as the cytoplasmic KKXX (SEQ ID NO:17) or RR of Teasdale and Jackson (1996), may be used. The ER-targeting sequence may be a Kar2p retention mutant, e.g., as described in Copic et al. (2009). In some embodiments, the C-terminal sequence -VEKPFAIAKE (SEQ ID NO:18) described in Arber et al. (1992), may be used to promote localization to a subcompartment of the ER. Each of the foregoing references is incorporated by reference in its entirety.

Epitope Tag Sequences

A construct of the present invention may comprise one, two, or more epitope tag or immunotag sequences conjugated to or expressed as a fusion protein with the substrate target on the surface of a cell (e.g., a yeast cell). It is anticipated that virtually any epitope tag may be used in various embodiments of the present invention. For example, epitope tags that may be included in a peptide or encoded by a nucleic acid of the present invention include, e.g., FLAG, 6× His, hemagglutinin (HA), HIS, c-Myc, VSV-G, V5 HSV, and any peptide sequence for which a monoclonal antibody is available. Antibodies that selectively bind the epitope tag sequences may be used to detect the presence or absence of the epitope tag(s); for example, a first antibody with a first fluorophore may be used to detect the presence or absence of a first epitope tag sequence, a second antibody with a second fluorophore may be used to detect the presence or absence of a second epitope tag sequence, and additional antibodies may be used to detect the presence or absence of a third, or more epitope tag, as desired. In some embodiments, the antibodies are labeled with a dye, such as a fluorophore, and used for cell sorting. As would be appreciated by one of skill in the art, a wide variety of antibodies that selectively recognize an epitope tag and are labeled with a detectable label such as a fluorophore are commercially available. Antibodies that selectively bind different epitope tags may be labeled with different fluorophores; in this way, cells may be separated or purified based on the presence or absence of one, two, three, or more fluorescent signals, e.g., using ratiometric FACS.

A wide variety of epitope tags have been engineered into recombinant proteins and may be used in various embodiments of the present invention. Epitope tags that may be used include, e.g., FLAG®, HA, HIS, c-Myc, VSV-G, V5, and HSV. Select epitope tags that may be used with the present invention are listed below.

TABLE 2

Select Epitope Tag Sequences

| Tag | Sequence | SEQ ID NO: |
|---|---|---|
| HIS | HHHHHH | SEQ ID NO: 11 |
| c-MYC | EQKLISEEDL | SEQ ID NO: 19 |
| HA | YPYDVPDYA | SEQ ID NO: 20 |
| VSV-G | YTDIEMNRLGK | SEQ ID NO: 21 |
| HSV | QPELAPEDPED | SEQ ID NO: 22 |
| V5 | GKPIPNPLLGLDST | SEQ ID NO: 23 |
| FLAG | DYKDDDDK | SEQ ID NO: 9 |

Cell Surface Display Sequence

The construct may comprise a sequence for expression on the cell surface. For example, after Golgi-derived vesicle to plasma membrane fusion occurs where the vesicle contains a substrate (containing a ER targeting sequence and an ER retention sequence), a cell-surface display sequence may be used to retain an amino acid (e.g., comprising one or more phosphorylated or unphosphorylated substrate sequences) on the surface of a eukaryotic cell, such as, e.g., a yeast cell.

In some embodiments, an Aga2p sequence can be used to display an amino acid sequence, such as a cleaved or uncleaved substrate amino acid sequence, on the surface of a eukaryotic cell, such as a yeast. For example, yeast cells can display a substrate from a randomized library extracellularly as a fusion to the Aga2p cell surface mating factor, which is covalently bound to the Aga1p mating factor via disulfide bonds (e.g., see FIG. 2). Expression of a fusion construct comprising Aga2p on the surface of yeast. Aga2p is an adhesin protein that is involved in agglutinin interaction mediated by Aga1p-Aga2p complexes and Sag1p (Huang et al., 2009), and Aga2p may be used for extracellular expression of a fusion protein in yeast (e.g., Kim et al., 2010; Boder and Wittrup, 1997). The Aga2p approach for expression of fusion proteins on the surface of yeast may be used for expression of a wide variety of proteins (Gai et al., 2007).

In other embodiments, an amino acid sequence, such as a phosphorylated or unphosphorylated substrate, may be displayed on the cell surface of a cell, such as a yeast using a glycosylphosphatidylinositol (GPI) anchor attachment signal sequence.

A mammalian mannose type Man5GlcNAc2 N-linked glycans may also be used to display a substrate. For example, a glycoengineered *Pichia pastoris* host strain that is genetically modified to secrete glycoproteins may be particularly useful for displaying a glycoprotein via this method as described, e.g., in Lin et al. (2011). This surface display method may use a linker (e.g., a pair of coiled-coil peptides) while using a GPI-anchored cell surface protein as an anchoring domain, such as, e.g., the *Saccharomyces cerevisiae* Sed1p GPI-anchored cell surface protein.

A self-assembled amyloid-like oligomeric-cohesin scaffoldin may be used for protein display on a yeast, such as, e.g., *Saccharomyces cerevisiae*. For example, the cellulosomal scaffolding protein cohesin and its upstream hydrophilic domain (HD) may be genetically fused with the yeast Ure2p N-terminal fibrillogenic domain consisting of residues 1 to 80 (Ure2p1-80). The resulting Ure2p1-80-HD-cohesin fusion protein may be expressed in *Escherichia coli* to produce self-assembled supramolecular nanofibrils that can serve as a protein scaffold. The excess cohesin units on the nanofibrils provide ample sites for binding to dockerin fusion protein, such as a dockerin-substrate fusion protein. Self-assembled supramolecular cohesin nanofibrils created by fusion with the yeast Ure2p fibrillogenic domain can provide a protein scaffold that can be effectively used for yeast cell surface display. Related methods are described in additional detail in Han et al. (2012).

In some embodiments, the construct may comprise an Aga2p sequence. The Aga2p yeast display system (Boder and Wittrup, 1997) has been previously characterized and may be used in various aspects of the present invention. Non-limiting examples of proteins that may be used as cell-surface proteins are described in Chen et al. (2011); Lee et al. (2011); Lin et al. (2012); Han et al. (2012); Gai et al. (2007); and article in press as: Gera et al. (2012), each of which are incorporated by reference in their entirety.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques. In certain preferred embodiments, the vector can express a nucleic acid sequence in a eukaryotic cell, such as, e.g., a yeast cell.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, such as those described herein.

An expression vector may comprise, for example, one or two or more promoters, enhancers, initiation signals, internal ribosome binding sites, multiple cloning site (MCS), RNA splicing sites, termination signals, polyadenylation signals, origins of replication (often termed "ori"), or selectable or screenable markers.

IV. EXPRESSION IN EUKARYOTIC CELLS

In certain aspects of the present invention, a kinase and kinase substrate may be expressed in eukaryotic cells in the presence of a kinase inhibitor. Cells that may be used with the present invention include, e.g., yeast, mammalian cells, insect cells, stem cells, human cells, primate cells, induced pluripotent stem cells, cancerous cells, and embryonic cell lines (e.g., HEK 293 cells, etc.). In some embodiments, yeast cells are used. In some embodiments, the yeast cells are Kex2 (−/−) knockout yeast cells. In some embodiments, the yeast has one, two, or all of the SNQ2, YOR1, and/or PDQ5 genes knocked out. SNQ2, YOR1, and PDQ5 can function as small molecule transporters, and by knocking out one or more of these genes (e.g., in a yeast) it may be possible to reduce the export of a kinase inhibitor from the cell. It is anticipated that, in various embodiments, virtually any cell that contains an endoplasmic reticulum (ER) may be used to selectively target a kinase and a substrate to the ER of the cell.

Using eukaryotic cells, such as yeast, for expression of a protein or enzyme of interest can offer significant advantages over using bacteria. For example, in view of previous experience with *E. coli*-based protease engineering systems (Varadarajan et al., 2008) as well as yeast surface expression (Boder and Wittrup, 1997), the YESS approach uses eukaryotic cells and thus can offer several potential advantages for identifying mutant kinases that are resistant to a kinase inhibitor. For example, the eukaryotic expression machinery in yeast can be more compatible with mammalian kinases, especially human kinases, as compared with bacteria, such as *E. coli*.

In some embodiments, yeast cells are used for selection of a mutant kinase that is resistant to a kinase inhibitor. Yeast cells may in some embodiments be advantageously used since, e.g., they are capable of dividing quickly and are relatively robust and allow for a reasonably simple culture. Yeast cell lines that may be used with the present invention include, e.g., GS115 cells, INVSc1 cells, KM71H cells, SMD1168 cells, SMD1168H cells, and X-33 cells. It is anticipated that virtually any strain of yeast may be used with the present invention. In some embodiments the yeast may be, e.g., *Saccharomyces cerevisiae* or *Pichia pastoris*. The yeast may be an Ascomycota, such as a Saccharomycotina (referred to as "true yeasts"), or a Taphrinomycotina, such as Schizosaccharomycetales (the "fission yeasts").

Various insect cell lines may be used with the present invention. For example, insect cells that may be used with the present invention include, e.g., *Drosophila* cells, Sf9 cells, and Sf21 cells.

Mammalian cell lines that may be used with the present invention include, e.g., HEK 293 cells, CHO cells, 3T3 cells, BHK cells, CV1 cells, Jurkat cells, and HeLa cells. In some embodiments, a human cell line may be used.

V. CELL SORTING

Cells may be sorted based on the presence of one or more sequences on the surface of the cell. For example, cells may be sorted using fluorescence-activated cell sorting (FACS) or magnetic-activated cell sorting (MACS).

Subsequent to cell sorting, the specific kinase (e.g., one or more mutant kinases that are resistant to a kinase inhibitor) produced by a yeast may be determined by genotyping nucleic acids from a colony of the yeast. A variety of known methods may be used for nucleotide sequencing. Virtually any sequencing method, such as, for example, traditional methods of sequencing or next-generation sequencing methods, may be used to determine the sequence of a kinase expressed in a cell. In some embodiments, the nucleotide sequencing can be determined, e.g., by pyrosequencing or by chain termination sequencing. In some preferred embodiments, the mutant kinase is sequenced using a next-generation sequencing methodology. For example, in some embodiments, Nanopore or PacBio® sequencing may be used in order to sequence multiple mutations over a larger portion of the mutant kinase.

Magnetic-Activated Cell Sorting (MACS)

Cells that selectively express a phosphorylated sequence on the surface of the cells (e.g., phosphorylated by a kinase expressed by the cell) may be isolated or separated from other cells using a magnetic-activated cell sorter (MACS). MACS typically utilizes an antibody (e.g., an antibody that selectively binds an epitope tag sequence located within an expressed protein or peptide), in combination with magnetic beads to separate cells over a column. MACS may, in certain embodiments, be relatively gentle on cells and favorably affect cell viability and integrity of certain mammalian cell lines as compared to FACS.

Various MACS products are commercially available, including MACS MicroBeads™ columns or AutoMACS™ (Miltenyi Biotec, CA, USA), and may be used according to the manufacturer's instructions. PBS/0.5% BSA (without EDTA) may used as the buffer for cell isolation. In some experiments, a Dead Cell Removal Kit (Miltenyi Biotec) may be used to remove dead cells prior to isolation of cells that express a cleaved target sequence. Repeated MACS columns may be used if necessary.

Fluorescence-Activated Cell Sorting (FACS)

Fluorescence-activated cell sorting (FACS) may also be used to separate cells that express a phosphorylated substrate sequence. FACS utilizes the degree of fluorescence exhibited by a cell to separate cells. In certain embodiments, antibodies comprising different fluorescent labels may be used to separate or purify a cell, such as a yeast cell, that expresses a phosphorylated substrate on the surface of the cell (e.g., indicating the presence of a mutant kinase that is able to phosphorylate an amino acid in a substrate sequence in the presence of a kinase inhibitor).

In some embodiments, FACS screening or other automated flow cytometric techniques may be used for the efficient isolation of a eukaryotic cell (e.g., a yeast cell) comprising a mutant kinase. Instruments for carrying out flow cytometry are known to those of skill in the art and are commercially available to the public. Examples of such instruments include FACStar™ Plus, FACScan™, and FACSort™ instruments from Becton Dickinson (Foster City, Calif.), Epics C from Coulter Epics Division (Hialeah, FA), and MOFLO™ from Cytomation (Colorado Springs, Colo.).

FACS may be used for sorting of cells. In various embodiments, the presence or absence of 1, 2, or more antibodies, which recognize 1, 2, or more epitope tags, amino acid sequences, or phosphorylated amino acids on the surface of a cell, reflects the activity of a kinase. FACS may also be used to separate cells that have been transformed with a desired construct from cells that do not contain or have not been transformed with a desired construct.

Flow cytometric techniques in general involve the separation of cells or other particles in a liquid sample. Typically, the purpose of flow cytometry is to analyze the separated particles for one or more characteristics, such as, e.g., presence of a labeled ligand or other molecule. FACS generally involves the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparatuses permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls.

FACS is described further, e.g., in U.S. Pat. Nos. 3,826,364; 4,284,412; 4,989,977; 4,498,766; 5,478,722; 4,857,451; 4,774,189; 4,767,206; 4,714,682; 5,160,974; and 4,661,913, each of which are specifically incorporated herein by reference.

In some embodiments, flow cytometry can be used repeatedly during multiple rounds of screening that are carried out sequentially. Cells may be isolated from an initial round of sorting and immediately reintroduced into the flow cytometer and screened again to improve the stringency of the screen. In some embodiments, non-viable cells can be advantageously recovered or separated using flow cytometry. Since flow cytometry generally involves a particle sorting technology, the ability of a cell to grow or propagate is not necessary in various embodiments of the present invention. Techniques for the recovery of nucleic acids from such non-viable cells are well known in the art and may include, for example, use of template-dependent amplification techniques, including PCR.

Bioreactors and Robotic Automation

One or more steps for the culture or separation of cells may be automated. Automating a process using robotic or other automation can allow for more efficient and economical methods for the production, culture, and differentiation of cells. For example, robotic automation may be utilized in conjunction with one or more of the culture of eukaryotic cells, passaging, addition of media, and separation of cells expressing a cleaved or uncleaved substrate, e.g., using MACS or FACS.

A bioreactor may also be used in conjunction with the present invention to culture or maintain cells. Bioreactors provide the advantage of allowing for the "scaling up" of a process in order to produce an increased amount of cells. Various bioreactors may be used with the present invention, including batch bioreactors, fed batch bioreactors, continuous bioreactors (e.g., a continuous stirred-tank reactor model), and/or a chemostat. A bioreactor may be used, e.g., to produce increased numbers of eukaryotic cells, such as yeast.

VI. NEXT GENERATION SEQUENCING

A variety of next generation-sequencing systems may be used with the present invention include. For example, the next-generation sequencer may utilize single-molecule real-time sequencing (e.g., produced by Pacific Biosciences, Menlo Park, Calif.), an ion semiconductor method (e.g., Ion Proton™, Ion PGM™), a pyrosequencing method (e.g., 454), a sequencing by synthesis method (e.g., an Illumina™ sequencer), or a sequencing by ligation method (e.g., a SOLiD™ sequencer). In some embodiments, the next generation sequencer is an Illumina™ sequencing system, or an Ion Torrent system (e.g., the Ion Proton™ Sequencer or the Ion PGM™ sequencer) from Life Technologies (Carlsbad, Calif., USA), SOLID, SOLID 2.0, 5500 Genetic Analyzer (e.g., 5500, 5500 W, etc.; Life Technologies, Carlsbad, Calif.) may be used in various embodiments of the present invention. In some embodiments, the next generation sequencer is a Pacific Biosciences system (e.g., the Sequel System or the PacBio RSII). In some embodiments, an automated method for sample preparation may be used; for example, the Ion Chef™ system may be used, e.g., in combination with an ion semiconductor sequencer such as, e.g., Ion Proton™ or Ion PGM™ (e.g., using the Ion 314™ Chip, Ion 316™ Chip, Ion 318™ Chip Ion PI™ Chip, or Ion PII™ Chip). Various Illumina systems are available and may be used in embodiments of the present invention such as, e.g., the HiSeq X Ten, HiSeq 2500, NextSeq 500, and MiSeq systems. The next-generation sequencing method may involve constructing a library by generating DNA, fragmenting the DNA, and then adding adaptors. Then the fragmented DNA may be amplified on beads, e.g., using emulsion PCR. In some embodiments, the next-generation sequencing method does not utilize beads (e.g., 5500 W, Illumina sequencers, etc.). It is anticipated that in some embodiments, amplification of sequences may be accomplished on a glass surface or solid support.

A. Data Analysis

Data obtained regarding the sequences of a resistant kinase, or a kinase that can continue to function in the presence of a kinase inhibitor, may be aligned with the sequence of the wild-type kinase in order to identify the mutations in the resistant kinase using a variety of alignment techniques and programs that are well-known in the art. In some embodiments, sequences comprising a stop codon may be excluded. Statistical analysis can be performed to identify the frequency of mutations which are associated with resistance of a kinase to a kinase inhibitor. In some embodiments, resistance mutations for a kinase may be compared to previously identified mutations that can also provide resistance against a kinase inhibitor. As shown in the below examples, the methods described herein can be used to identify resistance mutations that have been observed clinically in vivo.

In some embodiments, data analysis comprises trimming low-quality base calls from reads (e.g., based on Qphred quality scores below 25), and sequences are aligned to the wild-type sequence in order to identify mutations. Then, mutations may be translated into amino acid changes. The amino acid changes may be counted both individually and as they occur as compound mutations. The aligned and translated data of the unsorted pool may then be used to assess library quality and/or the data may be used as a baseline to calculate enrichment of mutations in the sorted libraries. In the case of comparing occurrences of compound mutations to single mutations, enrichment factors may in some instances be more informative because they can account for initial frequency of a particular mutation.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Vector Construction

Amino acids 237-630 of human ABL1 isoform 1 were cloned into the pESD vector (Yi et al. 2014) under the GAL10/GAL1 bidirectional promoter in place of TEV protease. For the library template vector, the TEV protease substrate was replaced with a minimal ABL substrate (AAAAAYAAAAA; SEQ ID NO:1). Yeast receptor adhesion subunit Aga2, ER retention signal, and hexahistidine (6-His) and FLAG epitope tags were retained from the pESD vector.

Validation of YESS-Based Inhibitor Resistance Assay

ABL wild-type and T315I mutant cultures were induced by growth in SG-UT medium containing 125 µM Dasatinib, Ponatinib, or equivalent volume of DMSO. After 40 hours of growth at 20 deg C, cells were washed three times with TBS+0.5% BSA+0.05% Tween20. Cells were stained with anti-His6-FITC (ThermoFisher) and anti-phosphotyrosine-PE (BioLegend) at 4 °C. for 30 minutes, followed by three washes with TBS+0.5% BSA+0.05% tween20. FACS analysis was performed on either the FACS Aria Ilu or FACSCalibur™ (BD Biosciences).

Error-Prone Library Construction

ABL kinase was amplified with primers JT017 (5'-ACCTCTATACTTTAACGTCAAGGAG-3'; SEQ ID NO:2) and JT119 (5-'GGTAACGGAACGAAAAATAGAAAAGGATATTACATGGG-3'; SEQ ID NO:24) to produce a 1550 bp product. A12 polymerase, an error-prone variant of KOD polymerase, was used for amplification to generate a pool of mutants (FIG. 1). Vector was prepared by digestion with SalI-HF, XhoI, and NcoI-HF. PCR product and digested vector were column purified and drop dialyzed in ddH$_2$O on VSWP membranes for one hour. Electrocompetent EBY100 were prepared as described previously (Yi et al. 2014; Boder and Wittrup 1997; Benatuil et al., 2010; Perez et al., 2010). In each of three 2 mm electroporation cuvette, 350 µl electrocompetent EBY100 were combined with 10 µg PCR product from error prone PCR and 3 µg digested pESD-derived vector to a maximum volume of 400 µl (FIG. 1). Transformed cells were passaged in SD-UT medium three times before proceeding to sorting experiments. Library size was estimated by colony counts from dilution series of transformed cells plated on SD-UT agar. Sanger sequencing was carried out on 32 randomly selected clones, as well as high throughput sequencing (described below) on an aliquot of the entire sample.

Library Screening by FACS

Library cells were induced by growth in 10 mL SG-UT with 25 µM inhibitor or equivalent volume of DMSO. 5×10$^7$ cells were washed with TBS+BSA then stained with anti-His6-FITC and anti-pY-PE for 30 minutes at 4° C. Cells were washed three times to remove unbound antibody. Wild-type ABL with and without inhibitor was used to determine the location of the sorting gates. PE+/FITC+ cells were sorted and re-sorted, then transferred to SD-UT medium for growth at 30° C. until dense, 1-2 days depending on number of cells collected (FIG. 1B). Subsequent rounds were performed identically until PE+/FITC+ cells accounted for 60-90% of the population.

High-Throughput Sequencing

Plasmids were recovered from saturated overnight cultures using ZymoPrep II kit (Zymo Research). DNA from unsorted, Dasatinib-, and Ponatinib-sorted libraries was barcoded on both ends using primers with identical annealing sequences but unique 16-mer sequences. After barcoding PCR, concentrations were quantified by Qubit and samples were pooled in equimolar ratios. Samples were sequenced using the PacBio RSII at the Arizona Genomics Institute at the University of Arizona in order to generate long reads so as to identify any compound mutations in the same clone (FIG. 1B).

Sequence Analysis

Sequences were assigned to their origin based on barcodes. Those without a 5' or a 3' barcode were discarded. Sequences were aligned to wild-type ABL kinase domain using an implementation of NCBI BLAST on the Texas Advanced Computing Core. Mutations in aligned sequences were then translated and compiled into a database.

YESS Validation of Resistant Mutants

Mutations to be validated were selected from the most frequently recovered sequences in each pool. Mutations were then introduced using mismatched primers followed by overlap-extension PCR. Sequence-validated clones were then grown overnight in SD-UT medium followed by induction in SG-UT medium with 25 µM inhibitor or DMSO for two days at 20° C. Cells were stained as previously described and analyzed on a FACSCalibur™ HTS (FIG. 1C).

In Vitro Validation of Resistant Mutants

ABL kinase domain (AA 229-511) was expressed as previously described (Kuriyan, Protein Science). Cleared cell lysate was applied to 2 mL equilibrated Ni-NTA resin in a gravity-flow column. Elution fractions were dialyzed overnight into QA buffer (Kuriyan, Protein Science), followed by anion-exchange purification with a Mono Q 5/50 GL column (GE Life Science). Kinetic activity was assayed by incorporation of [γ-$^{32}$P]-ATP (Sigma Aldrich) into the known substrate ABLtide (AnaSpec). Reactions contained 200 µM ABLtide, 100 mM Tris pH8.0, 10 mM $MgCl_2$, and 2 mM DTT. $K_m$(ATP) was first determined using saturating substrate (200 µM), followed by $K_i$ determination with [ATP] at $K_m$(ATP).

Ba/F3 Validation of Resistance Mutants

Figure 5:
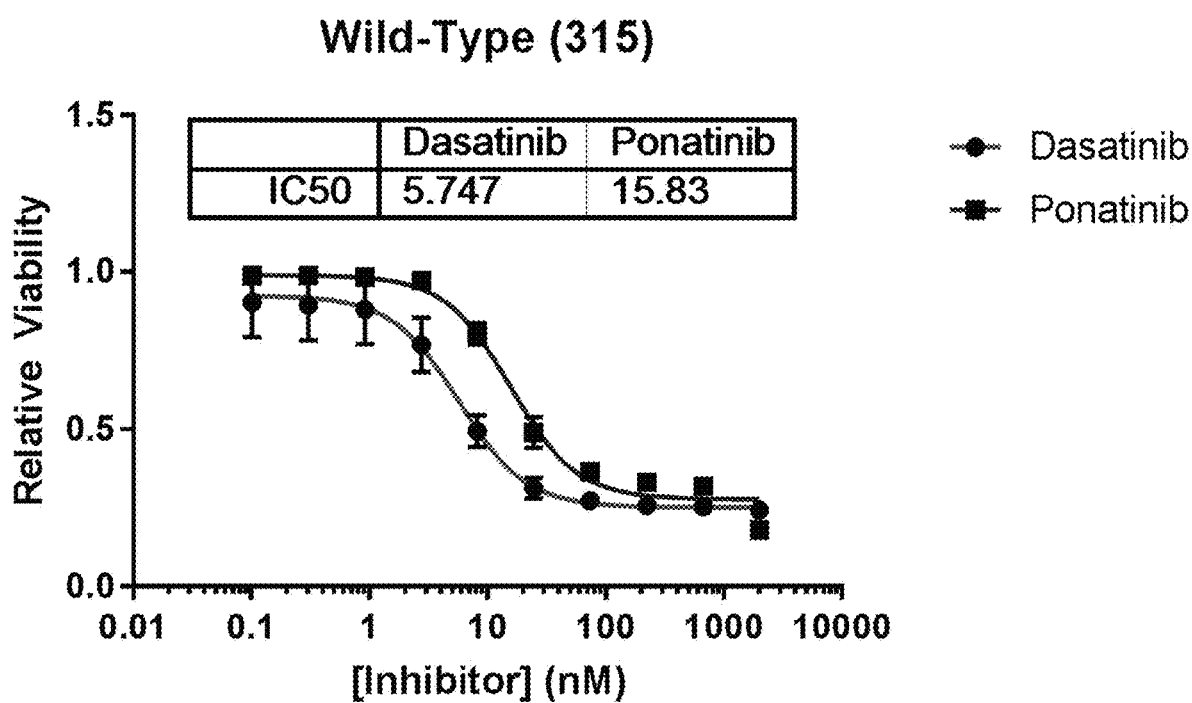
FIG. 5: In vitro validation of selected mutants. Ponatanib-selected mutants were cloned into full-length BCR-ABL retroviral vectors and integrated into the Ba/F3 murine pro-B cell line. Two of four single-mutants and two of three double-mutants had significantly higher $IC_{50}$ values than compared to wild-type ABL.
Figure 5:
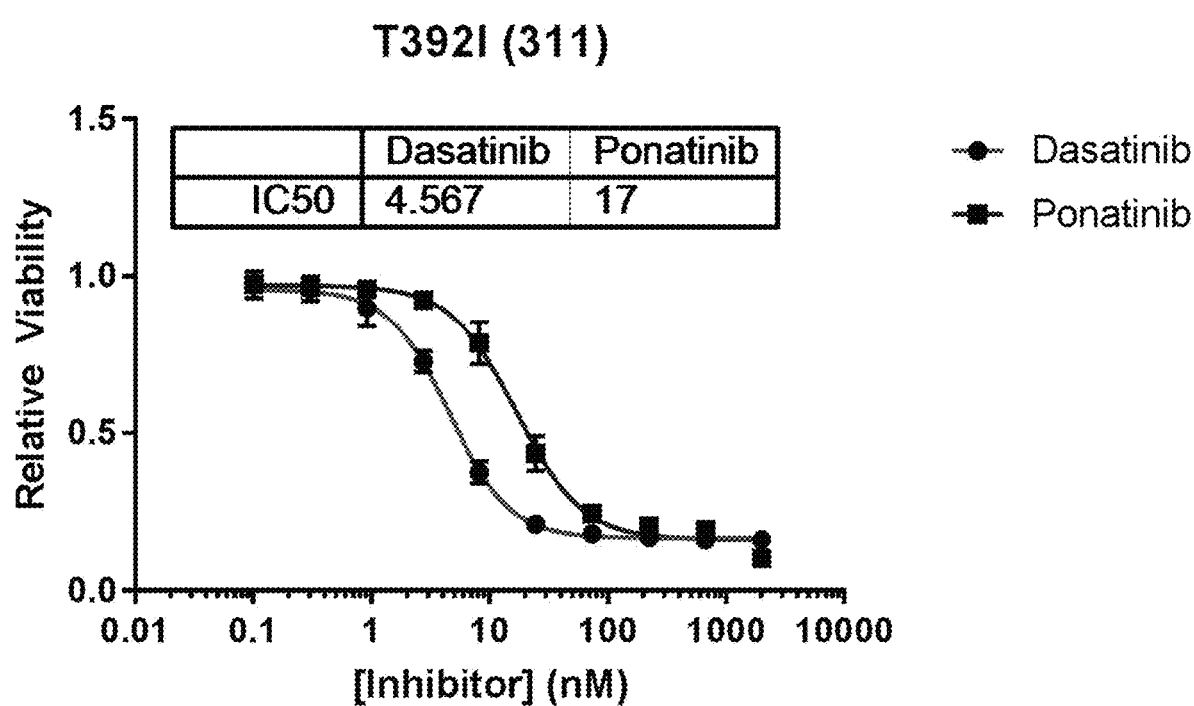

BCR/ABL-transduced Ba/F3 cells were grown in RPMI medium (Lonza) supplemented with 10% FBS, 100 U/mL penicillin, and 100 ug/mL streptomycin. Cells thawed from freezer stocks were passaged twice in media additionally supplemented with 10 ng/mL IL-3 (Peprotech), followed by two passages in the absence of IL-3. $5 \times 10^4$ cells were seeded in 100 µl in each well of a 96-well plate. 50 µl of inhibitor diluted in RPMI+FBS+Pen/Strep was added to each well. After 24 hours, cell viability was quantified using the CellTiter Glo kit (Promega) according to manufacturer's instructions, with the exception that the reagent was diluted 1:5 in sterile PBS. Luminescence was detected using 96-well plate reader (Tecan). Titraiton curves were fitted using a four-parameter dose-response curve using GraphPad Prism (FIG. 5).

Example 2

Identification of Resistant Mutants

Validation of YESS-Based Inhibitor Resistance Assay

Figure 2:
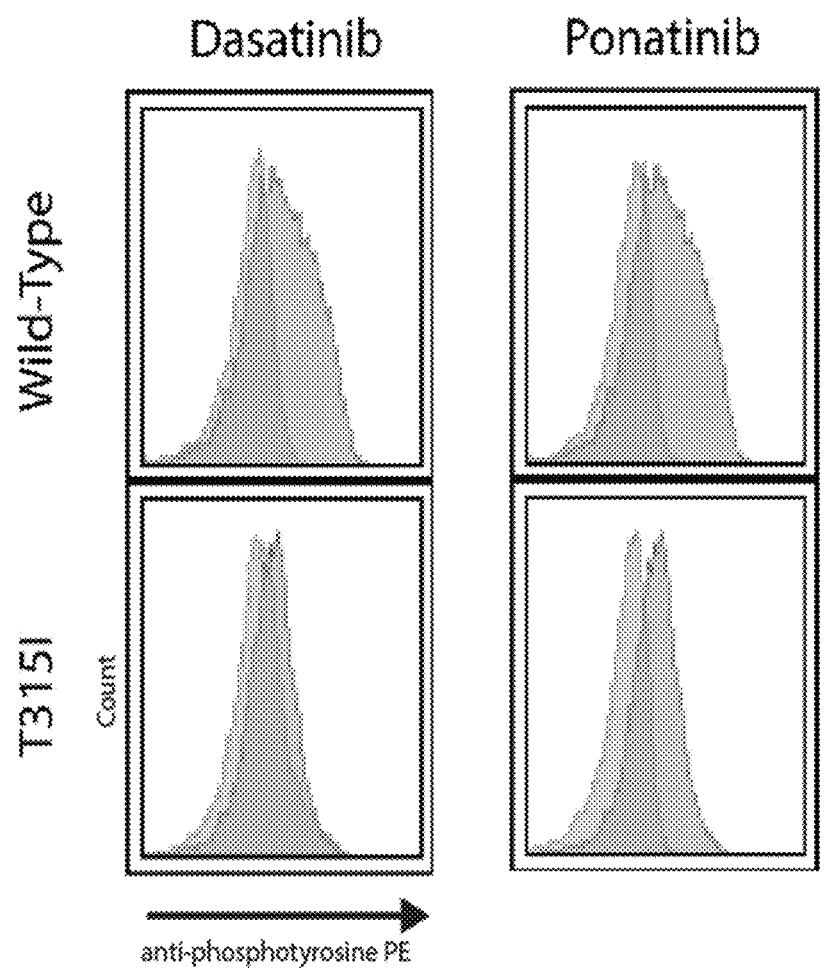
FIG. 2: Inhibition of wild-type ABL kinase and T315I ABL kinase by Dasatinib and Ponatinib.
Figure 3:
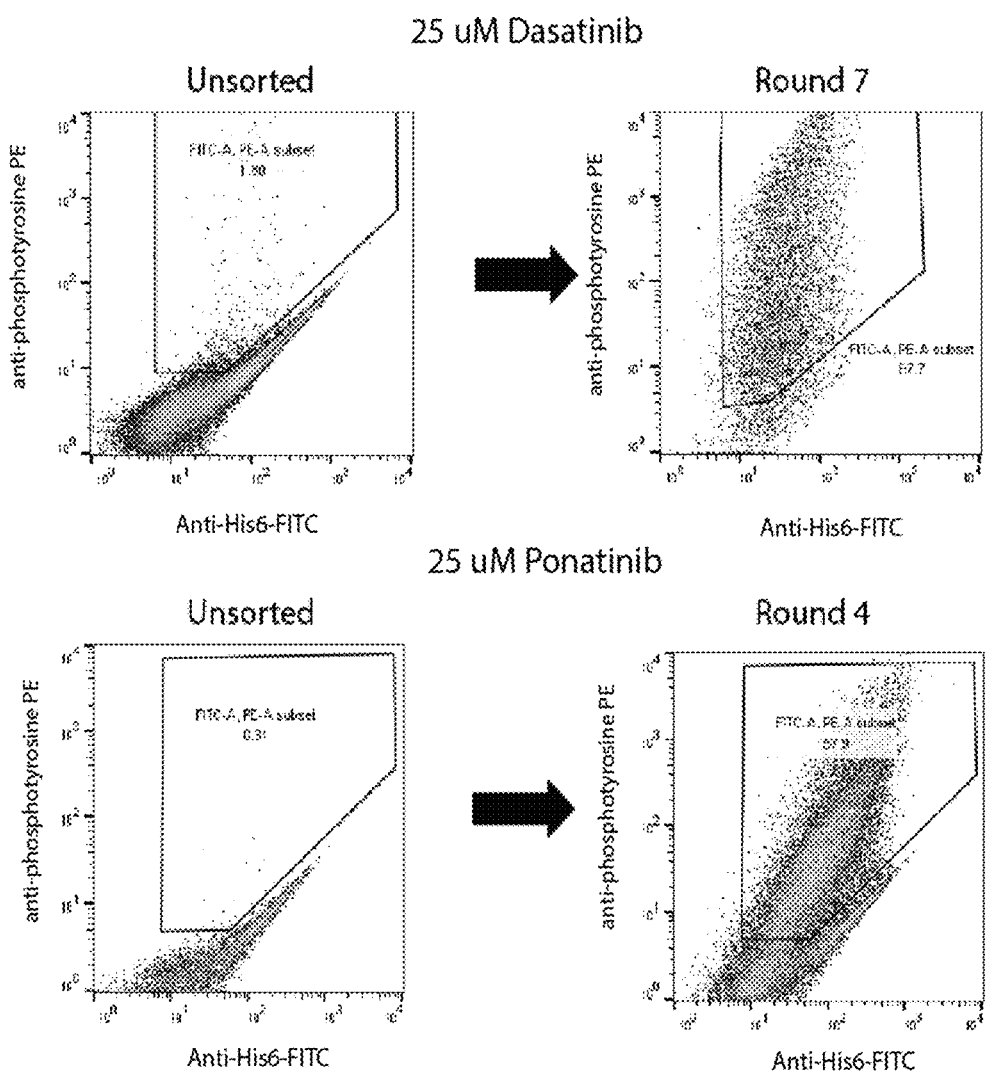
FIG. 3: Enrichment of inhibitor resistance clones by FACS.

FACS analysis of wild-type ABL kinase expressing cells showed a decrease in PE fluorescence in the presence of 125 µM Dasatinib or Ponatinib compared to DMSO only. ABL T315I expressing cells showed a decrease in PE signal in the presence of Ponatinib but not Dasatinib compared to DMSO only (FIG. 2). These data correspond to known resistance of ABL T315I to inhibition by Dasatinib but not Ponatinib.

Error-Prone Library Construction

An error-prone library was created as described above. Library size was estimated to be $3.2 \times 10^7$ based on colony counts. This library size exceeds single point mutation diversity by approximately $10^4$-fold and double mutation diversity by two-fold. Sanger sequencing of 32 individual clones showed a mutation rate of 0.07%, or about one mutation per gene, on average. High-throughput sequencing generated approximately $2 \times 10^4$ sequence reads containing $1.4 \times 10^4$ mutations. 77% of all possible single nucleotide substitutions were observed.

Library Screening by FACS

The fraction of PE-positive cells in Dasatinib-treated cultures increased from 1.8% in the unsorted pool to 87.7% in the post-sort 6 sample. The fraction PE-positive cells in Ponatinib treated cultures increased from 0.31% in the unsorted pool to 57.9% of cells in the pre-sort 4 pool. $10^7$ Dasatinib-treated cells were sorted and $5 \times 10^4$ cells were collected in the first round. $3.3 \times 10^7$ Ponatinib-treated cells were sorted and $2.6 \times 10^4$ of these were collected in the first round. In subsequent rounds, the number of cells sorted always exceeded the first bottleneck by at least 10-fold.

Sequence Analysis

PacBio RSII returned approximately $10^4$ sequence reads for each of the three pools: unsorted library, Ponatinib-screened, and Dasatinib-screened. Due to the high-frequency of insertions and deletions in the PacBio data, sequences were aligned to the wild-type ABL kinase domain. In each case the sorted pools were highly polarized compared to the unsorted pool. In the Dasatinib-screened pool, the top 73 mutants composed over 80% of the observed sequences (Table 3, part A). In the Ponatinib-screened pool, the top 10 mutants composed over 80% of the observed sequences (Table 3, part B). In the unsorted library, the top 1250 mutants account for 80% of the observed sequences.

TABLE 3

Dasatinib and Ponatinib Screen Sequencing Results

| Rank | Mutations | Count | IC50 (nM) |
|---|---|---|---|
| A |  |  |  |
| Dasatinib Screen |  |  |  |
|  | Parental | 5623 | 0.8-5.6 |
| 1 | V448L | 1241 |  |
| 2 | E255V | 773 | 6.3-11 |
| 3 | F317L | 625 | 7.4-18 |
| 4 | G250E | 532 | 1.8-8.1 |
| 5 | Y253H | 524 | 1.3-10 |
| 6 | F493L | 422 |  |
| 7 | D455G | 347 |  |
| 8 | V448M | 306 |  |
| 9 | R239H | 198 |  |
| 10 | F401L | 157 |  |
| 11 | F497L | 143 |  |
| 12 | L384M | 122 | 4 |
| 13 | Q252H | 108 | 3.4-5.6 |
| 14 | F359I | 82 |  |
| 15 | V304A | 82 |  |
| 16 | E255V/V448L | 76 |  |
| 17 | V299L | 71 | 15.8-44.1 |
| 18 | F317L/V448L | 66 |  |
| 19 | Y253H/V448L | 59 |  |
| 20 | F317L/F493L | 57 |  |
| ... | ... | ... |  |
| 49 | T315I | 21 | 137->1000 |
| 52 | M244V | 20 | 1.3-3.6 |
| 383 | F359V | 3 | 2.2-2.7 |
| 423 | T392I | 2 | 4.57 |
| 716 | G303R | 1 | 41.92 |
| n/a | F311I | 0 | 2.7 |
| n/a | M351T | 0 | 1.1-1.6 |
| n/a | H396R | 0 | 1.3-3.0 |
| n/a | D325N | 0 | 5.84 |
| n/a | E255V/G303R | 0 | 38 |
| n/a | E255V/D325N | 0 | 32.78 |
| n/a | E255V/T392I | 0 | 7.3 |
| B |  |  |  |
| Ponatinib Screen |  |  |  |
|  | Parental | 1662 | 3.9-15.8 |
| 1 | E255V | 2605 | 41.9-55.6 |
| 2 | Y253H | 751 | 29.8 |
| 3 | E255V/M351L/G555D | 419 |  |
| 4 | E255V/M351L | 373 |  |
| 5 | E255V/G555D | 279 |  |
| 6 | E255V/E450G | 199 |  |
| 7 | Y253H/E255V | 182 | 203.5 |
| 8 | G303R | 172 | 89.8 |
| 9 | E255V/T392I | 109 | 40.5 |
| 10 | G555D | 83 |  |
| 11 | E255V/V448M | 79 |  |
| 12 | M351L | 73 |  |
| 13 | E255V/G303R | 70 | 56.1 |
| 14 | K285N | 67 |  |
| 15 | M351L/G555D | 55 |  |
| 16 | E255V/K415E | 47 |  |
| 17 | E255V/T597I | 46 |  |
| 18 | Y253H/G555D | 45 |  |
| 19 | G250E | 38 | 39.3 |
| 20 | E450G | 38 |  |
| ... | ... | ... |  |
| 24 | E255V/D325N | 31 | 294.2 |
| 35 | T392I | 18 | 17 |
| 73 | D325N | 8 | 21.2 |
| 103 | T315I | 5 | 29.1 |
| 230 | Q252H | 2 | 27 |
| 233 | M244V | 2 | 12.7 |
| n/a | V299L | 0 | 8.5 |
| n/a | F311I | 0 | 13.4 |
| n/a | F317L | 0 | 13.8 |

TABLE 3-continued

Dasatinib and Ponatinib Screen Sequencing Results

| Rank | Mutations | Count | IC50 (nM) |
|---|---|---|---|
| n/a | M351T | 0 | 9 |
| n/a | F359V | 0 | 22.7 |
| n/a | H396R | 0 | 20.1 |

Figure 4:
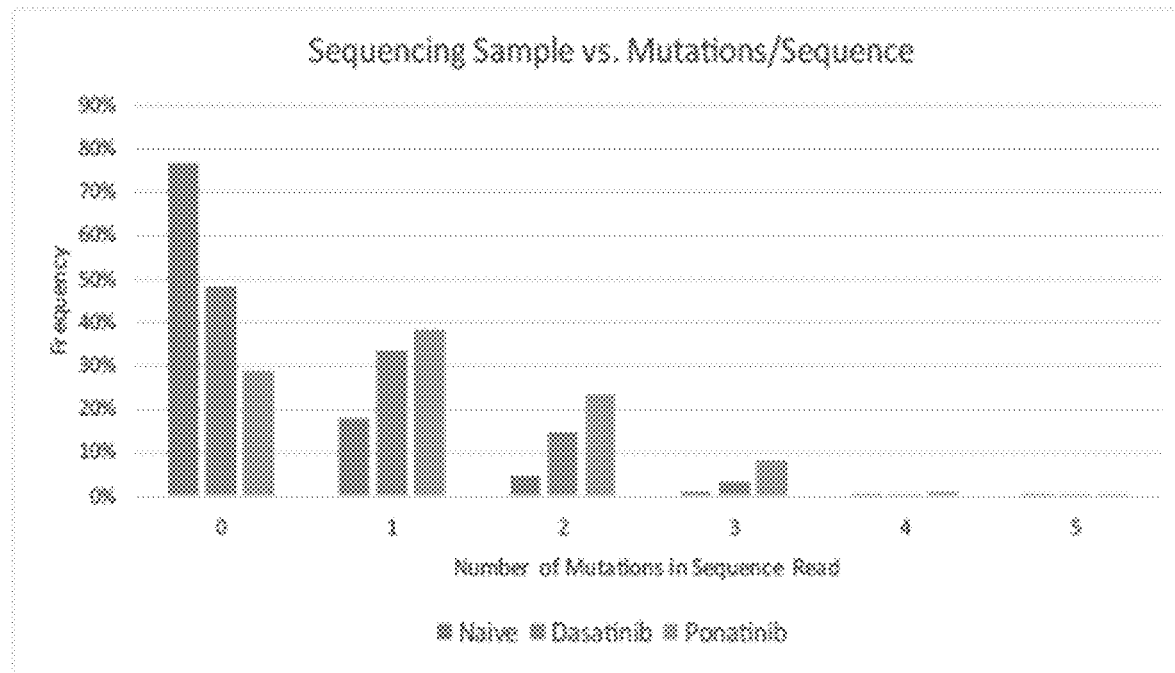
FIG. 4: Sequencing results. Underlined mutations indicate that the mutation has also been observed in vivo in patient populations that have become resistant to the kinase inhibitor.

The mutations recovered from this screen were compared to mutations seen in patients treated for CML. From the Dasatinib-screened pool, four of the five most frequent mutations observed are known mutations that have been recovered from CML patients (FIG. 4, top left). In the case of Ponatinib, all five of the common mutations from this data are known to be present in CML patients. In addition, six of the top 10 most common sequence reads from the Ponatinib-screened pool contained multiple mutations (FIG. 4, top right). 23% of all sequence reads contained two mutations, representing a 4-fold increase from the unsorted pool (FIG. 4, bottom). The presence of multiple mutations reflects data seen from CML patients with multiple mutations in the ABL gene. Double mutants have been show in vitro to be resistant to inhibition by Ponatinib, which is otherwise highly effective against single kinase inhibitor resistant mutations (Zabriske et al. 2014, Cell).

In Vitro Characterization of Mutants

Seven kinase-domain mutants selected for Ponatinib resistance and wild-type BCR-ABL were assayed for resistance to inhibition by Ponatinib in the murine Ba/F3 pro-B cell line. In particular, three common Ponatinib-resistant double mutation variants and the corresponding four constitutive single mutation analogs were assayed to investigate the importance of the compound mutations for Ponatinib resistance (FIG. 5). All three of the double mutants (E255V/G303R, E255V/D325N, E255V/T392I) assayed had a significantly higher $IC_{50}$ values for Ponatinib than wild-type. The two single mutants which were in the top 20 sequences (E255V, G303R) also displayed higher $IC_{50}$ values compared to wild-type, while the two single mutants which were not in the top 20 sequences did not have significantly higher $IC_{50}$ values for Ponatinib (D325N, T392I). The E255V/G303R double mutant was slightly less resistant than the single G303R mutation, but more resistant than the E255V mutation alone. The E255V mutation conferred a 2.5-fold increase in $IC_{50}$ for Ponatinib, while the D325N mutation alone was not significantly different from wild-type. However, when combined, these two mutations result in an $IC_{50}$ nearly 20-fold higher than wild-type. On the other hand, the E255V/T392I double mutant does not confer additional resistance compared to its most resistant constitutive mutation, E255V, while the T392I mutation alone is no more resistant than wild-type.

Example 3

Identification of Kinase Inhibitor Resistant BTK Mutants

Vector Construction

Figure 6:
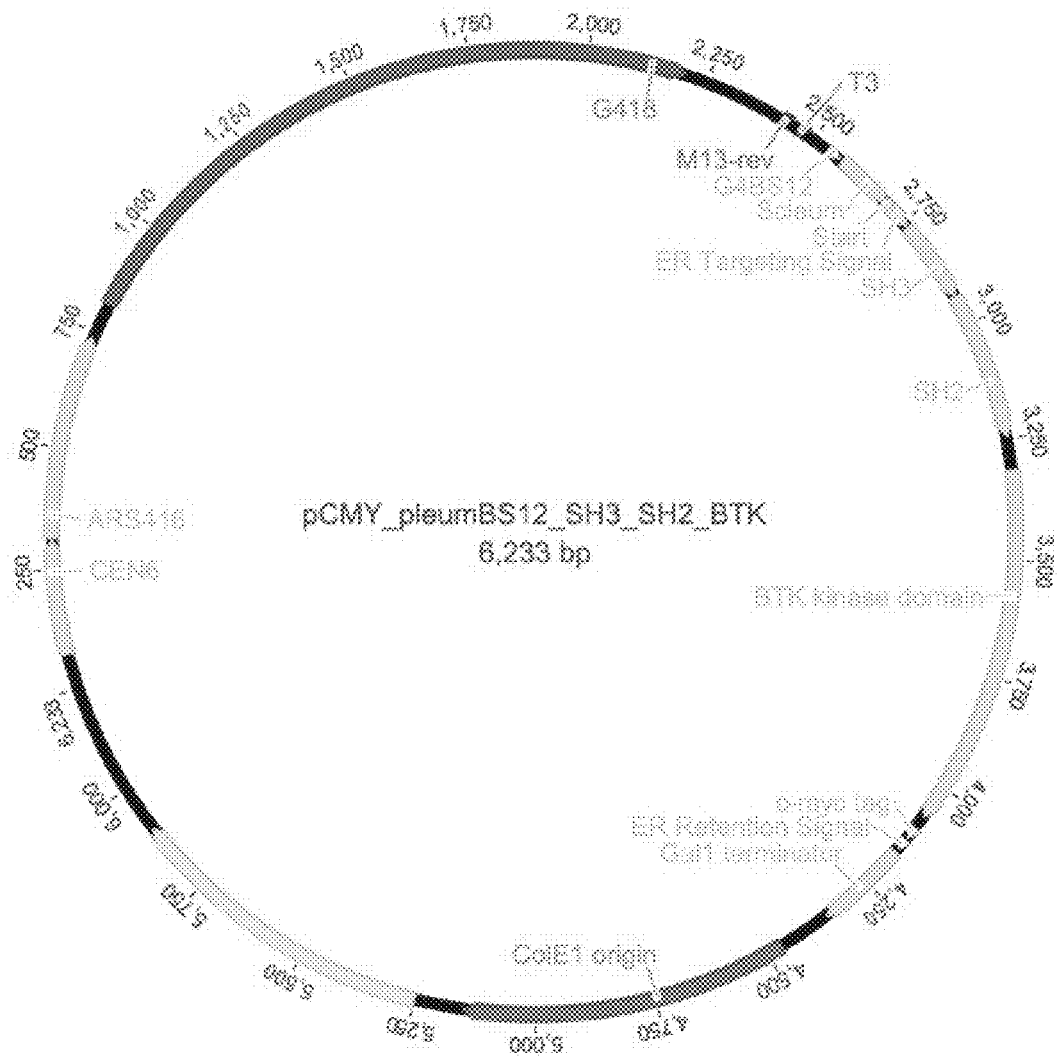
FIG. 6: Map of vector pCMYpLeumG4BS12_SH3_SH2_BTK.

Expressing BTK with the initial vector was toxic to Saccharomyces cerevisiae. This toxicity was overcome by expressing BTK using a weaker synthetic promoter taken from the p416leum-A2-G4BS12 plasmid (Blazeck et al. 2012). To accommodate this new promoter the kinase cassette and the displayed phospho-acceptor reporter cassette were split across two different plasmids. The kinase cassette including the promoter from p416leum-A2-G4BS12 plasmid and the nucleotide sequence encoding human BTK (217-655; i.e., Genbank reference number 695, amino acids 217-655, corresponding to nucleotides 649-1965) were subcloned into a plasmid containing the yeast CEN6 centromere, a yeast G418 resistance marker, an E. coli ColE1 origin of replication and an E. coli ampicillin resistance maker. This vector was referred to as: pCMYpLeumG4BS12_SH3_SH2_BTK (FIG. 6).

Figure 7:
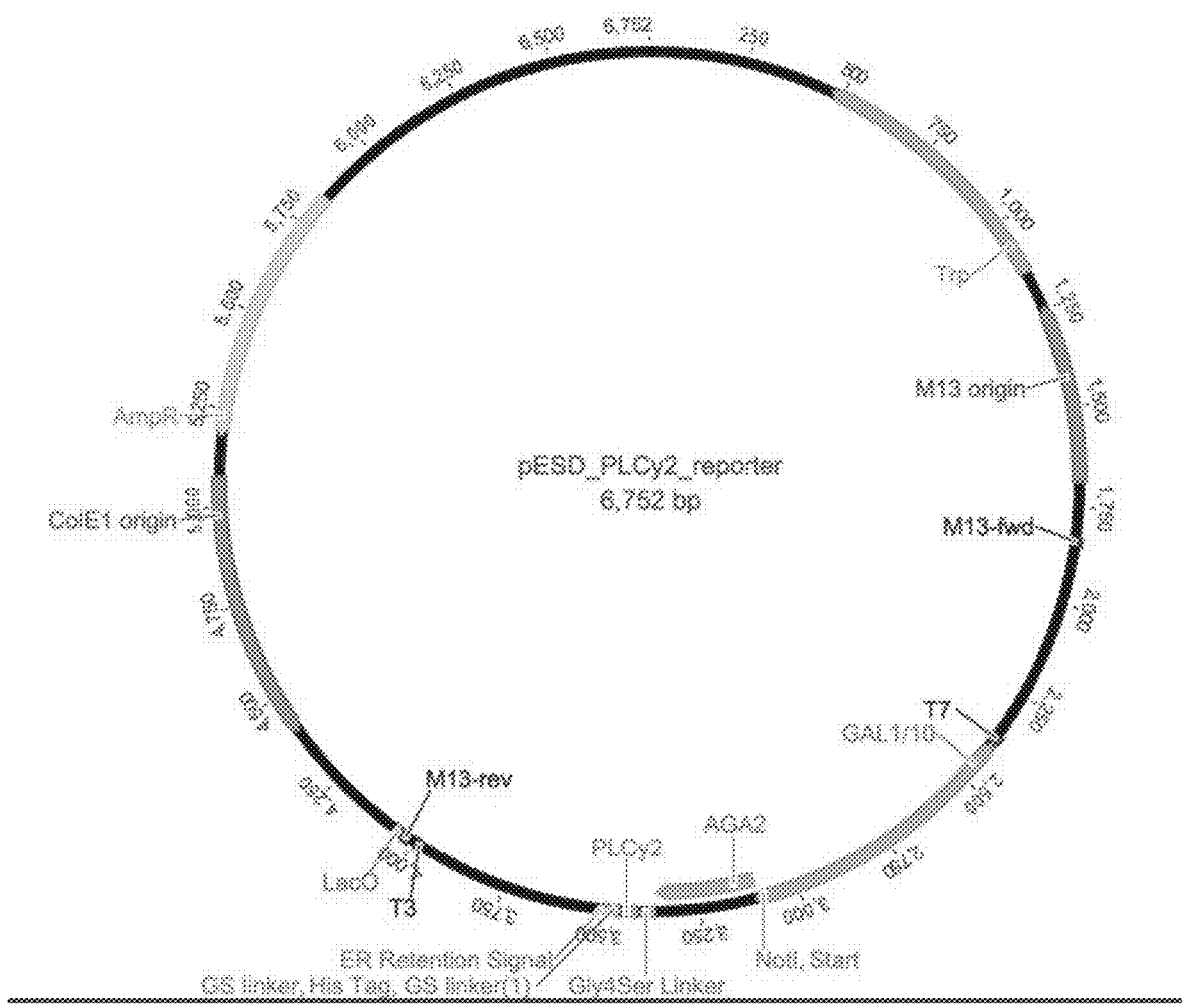
FIG. 7: Map of vector pESD_PLCγ2_reporter.

The phospho-acceptor reporter encodes the 18 amino acids (ERDINSLYDVSRMYVDPS, SEQ ID NO: 25) of 1-phosphatidylinositol 4,5-bisphosphate phosphodiesterase gamma-2 (PLCG2) which are phosphorylated by BTK. This vector was referred to as: pESD_PLCγ2_reporter (FIG. 7). Yeast receptor adhesion subunit Aga2, ER retention signal, and hexahistidine (6-His) and FLAG epitope tags were retained from the pESD vector.

Validation of YESS-Based Inhibitor Resistance Assay for BTK.

Figure 8:
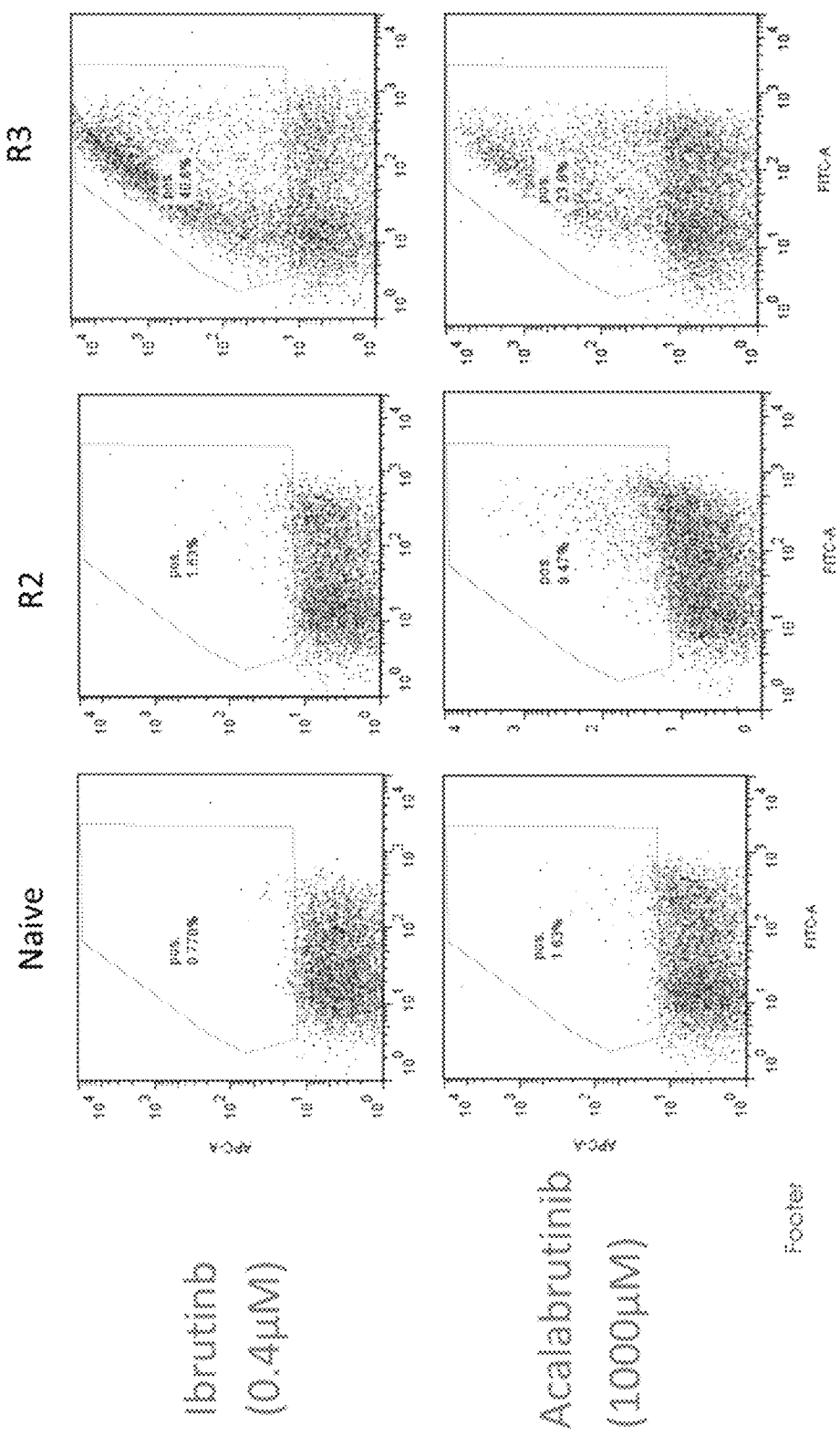
FIG. 8: subsequent rounds (Native, R2, R3) of YESS screening for resistant BTK mutants. Increased numbers of resistant mutants were identified in subsequent rounds of screening.

Human BTK (217-655) wild-type and C481S mutant cultures were induced by growth in SG-UT medium plus 100 µg/mL G418 containing 400 nM Ibrutinib, 1000 µM Acalabrutinib, or equivalent volume of DMSO. After 48 hours of growth at 25° C., cells were washed three times with TBS+0.5% BSA. Cells were stained with anti-His6-FITC (ThermoFisher) and Alexa Fluor® 647 anti-Phosphotyrosine Antibody (BioLegend) at 4 deg C for 30 minutes, followed by three washes with TBS+0.5% BSA. FACS analysis was performed on either the FACS Aria II (BD Biosciences). Results of subsequent rounds (Native, R2, R3) of YESS screening is shown in FIG. 8.

Error-Prone Library Construction

BTK (217-655) was amplified with primers JD1181 (5'-ATTAACGGAAGCTTcggattagaagccg-3'; SEQ ID NO: 26); and JD1185 (5'-gtgttactactcgttattattgcgtattttgtgatgc-3'; SEQ ID NO: 27) to produce a 1735 bp product. A12 polymerase, an error-prone variant of KOD polymerase, was used for amplification to generate a pool of mutants. Vector was prepared by digestion with XhoI and XbaI. PCR product and digested vector were gel extracted and drop dialyzed in ddH$_2$O on VSWP membranes for one hour. Electrocompetent EBY100 harboring the pESD_PLCγ2_reporter plasmid were prepared as described previously with the exception that YPD media was replaced with SD-UT to maintain the pESD_PLCγ2_reporter plasmid (Yi et al. 2014; Boder and Wittrup 1997; Benatuil et al., 2010; Perez et al., 2010)). In each of six 2 mm electroporation cuvette, 350 µl electrocompetent EBY100 cells harboring pESD_PLCy2_reporter were combined with 10 µg PCR product from error prone BTK PCR and 3 µg digested pCMYpLeumG4BS12_SH3_SH2_BTK vector to a maximum volume of 400 µl. Transformed cells recovered in SD-UT for 4 hours at 30° C. before they were passaged in SD-UT medium plus 100 µg/mL G418 two times before proceeding to sorting experiments. Library size was estimated by colony counts from dilution series of transformed cells plated on SD-UT agar plus 100 µg/mL G418. Sanger sequencing was carried out on 15 randomly selected clones, as well as high throughput sequencing (described below) on an aliquot of the entire sample.

Library Screening by FACS

Library cells were induced by growth at 25° C. for 45 hr in 50 mL SG-UT plus 100 µg/mL G418 with 400 nM Ibrutinib, 1000 µM Acalabrutinib or equivalent volume of DMSO. 3×10$^8$ cells were washed with TBS+BSA for each library and then stained with anti-His6-FITC and anti-pY-APC for 30 minutes at 4° C. Cells were washed three times to remove unbound antibody. Wild-type BTK (217-655) with and without inhibitor was used to determine the location of the sorting gates. APC+/FITC+ cells were sorted, then transferred to SD-UT medium plus 100 µg/mL G418 for growth at 30° C. until dense, 1-2 days depending on number of cells collected (FIG. 7).

High-Throughput Sequencing

Plasmids were recovered from saturated overnight cultures using ZymoPrep II kit (Zymo Research). DNA from unsorted, Ibrutinib-, and Acalabrutinib-sorted libraries were barcoded on both ends using primers with identical annealing sequences but unique 16-mer sequences. After barcoding PCR, concentrations were quantified by Qubit and samples were pooled in equimolar ratios. Samples were sequenced using the PacBio RSII at the University of California, Davis DNA Technologies Core in order to generate long reads.

Validation of YESS-Based Inhibitor Resistance Assay

Figure 9:
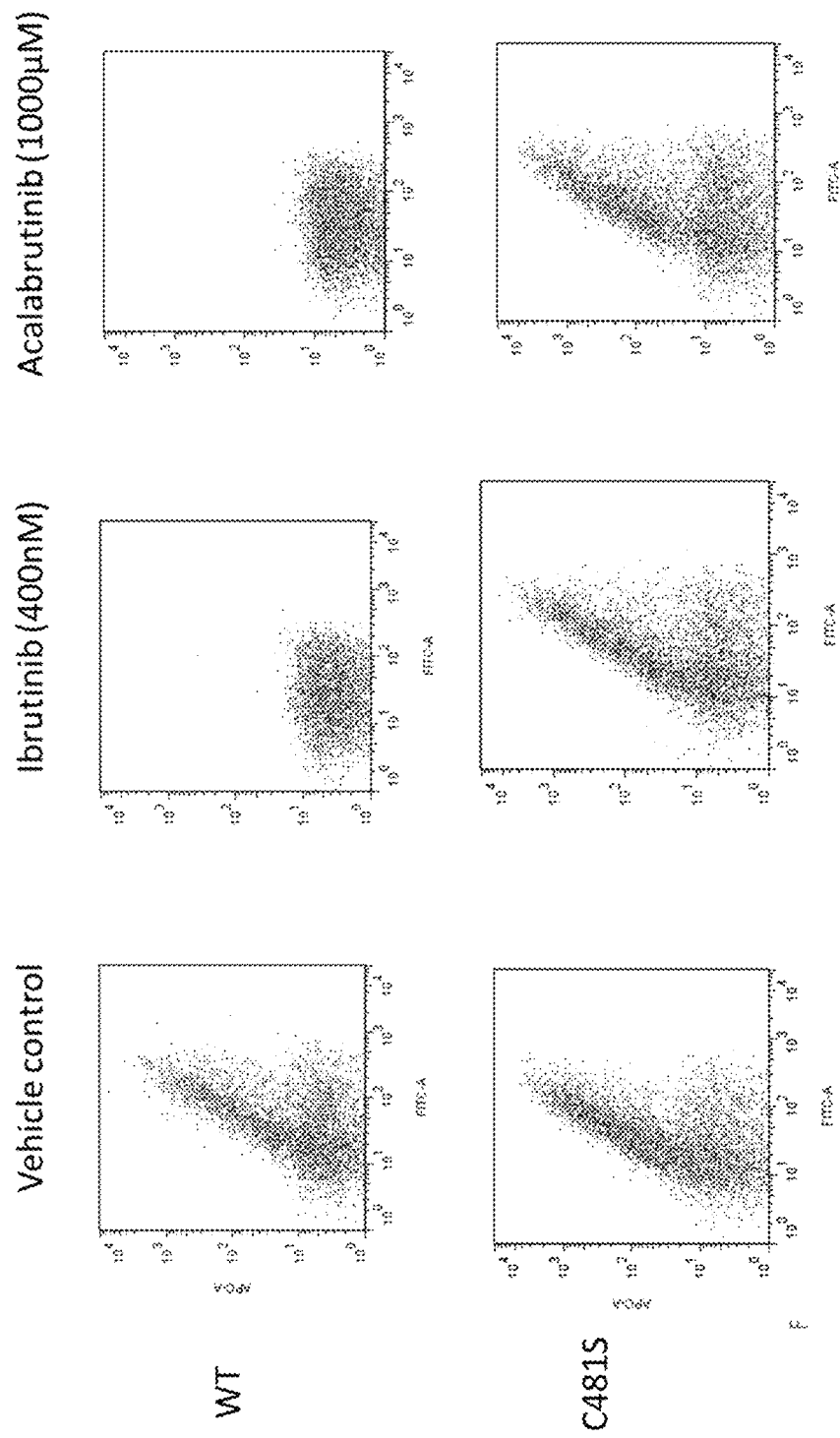
FIG. 9: BTK C481S expressing cells retained APC signal in the presence of Ibrutinib and Acalabrutinib compared to DMSO only

FACS analysis of wild-type human BTK kinase (217-655) was performed. Kinase expressing cells showed a decrease in APC fluorescence in the presence of 400 nM Ibrutinib or 1000 µM Acalabrutinib compared to DMSO only. BTK C481S expressing cells retained APC signal in the presence of Ibrutinib and Acalabrutinib compared to DMSO only (FIG. 9). These data correspond to known resistance of BTK C481S to inhibition by Ibrutinib and Acalabrutinib.

Error-Prone Library Construction

An error-prone library was created as described above. Library size was estimated to be $1.3 \times 10^7$ based on colony counts. This library size exceeds single point mutation diversity by approximately $10^4$-fold. Sanger sequencing of 16 individual clones showed a mutation rate of 0.08%, or about one mutation per gene, on average.

Library Screening by FACS

The fraction of APC-positive cells in Ibrutinib-treated cultures increased from 0.7% in the unsorted pool to 40.60% pre-sort round 3. The fraction of APC-positive cells in Acalabrutinib treated cultures increased from 1.63% in the unsorted pool to 23.8% of cells in the pre-sort round 3 pool. These collected cells were restained and resorted the same day to generate a pool of cells with kinase activity. $1.1 \times 10^8$ Ibrutinib-treated cells were sorted in the first round. $0.9 \times 10^8$ Acalabrutinib-treated cells were in the first round.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,498,766
U.S. Pat. No. 4,554,101
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,897,268
U.S. Pat. No. 4,989,977
U.S. Pat. No. 5,075,109
U.S. Pat. No. 5,160,974
U.S. Pat. No. 5,478,722
U.S. Pat. No. 5,552,157
U.S. Pat. No. 5,565,213
U.S. Pat. No. 5,567,434
U.S. Pat. No. 5,738,868
U.S. Pat. No. 5,795,587
U.S. Pat. No. 8,945,855
U.S. Pat. No. 9,546,359
PCT/US 15/55494
WO 2008/137475
WO 2014/004540 (PCT/US2013/047663)
Aharoni et al., *Chem. Biol.,* 12(12):1281-1289, 2005.
Arber et al., *J. Cell Biol.,* 116:113-125, 1992.
Aridor, M., and Hannan, L. (2000) Traffic jam: a compendium of human diseases that affect intracellular transport processes, Traffic (Copenhagen, Denmark) 1, 836-851.
Aridor, M., and Hannan, L. (2002) Traffic jams II: an update of diseases of intracellular transport, Traffic (Copenhagen, Denmark) 3, 781-790.
Beinfeld, M. (1998) Prohormone and proneuropeptide processing. Recent progress and future challenges, Endocrine 8, 1-5.
Benatuil et al., *Protein Eng. Des. Sel.,* 23(4):155-159, 2010.
Blazeck, J., et al., Controlling promoter strength and regulation in Saccharomyces cerevisiae using synthetic hybrid promoters. *Biotechnol Bioeng,* 109(11): p. 2884-95, 2012.
Boder and Wittrup, *Nat. Biotechnol.,* 15(6):553-557, 1997.
Bostian, K., Elliott, Q., Bussey, H., Burn, V., Smith, A., and Tipper, D. (1984) Sequence of the preprotoxin dsRNA gene of type I killer yeast: multiple processing events produce a two-component toxin, Cell 36, 741-751.
Boulware, K. T. and Daugherty, P. S. (2006) Protease specificity determination by using cellular libraries of peptide substrates (CLiPS), Proc. Nat. Acad. Sci., USA 103, 7583-7588.
Bourbonnais, Y., Ash, J., Daigle, M., and Thomas, D. (1993) Isolation and characterization of *S. cerevisiae* mutants defective in somatostatin expression: cloning and functional role of a yeast gene encoding an aspartyl protease in precursor processing at monobasic cleavage sites, The EMBO journal 12, 285-294.
Cawley, N., Chen, H., Beinfeld, M., and Loh, Y. (1996) Specificity and kinetic studies on the cleavage of various prohormone mono- and paired-basic residue sites by yeast aspartic protease 3, The Journal of biological chemistry 271, 4168-4176.
Chanalia et al., *Rev. Med. Microbiol.,* 22(4):6, 2011.
Chao et al., *Nat. Protoc.,* 1(2):755-768, 2006.
Chen et al., *Proc. Natl. Acad. Sci. USA,* 108(28):11399-11404, 2011.
Collen and Lijnen, *Blood,* 78(12):3114-3124, 1991.
Copic et al., *Genetics,* 182:757-769, 2009.
Craik et al., *Biochem. J.,* 435(1):1-16, 2011.
Denecke et al., *EMBO J.,* 11(6):2345-2355,
Diamond, S. (2007) Methods for mapping protease specificity, Current opinion in chemical biology 11, 46-51.

Dix, M. M., Simon, G. M., Cravatt, B. F., (2008) Global Mapping of the Topography and Magnitude of Proteolytic Events in Biological Systems, Cell 134, 679-691

Dougherty and Parks, *Virology*, 172145, 1989.

Dougherty et al., *Embo J.*, 7(5):1281-1287, 1988.

Dougherty et al., *Virology*, 172:302, 1989.

Drag and Salvesen, *Nat. Rev. Drug Discov.*, 9:690-701, 2010.

Drummond et al., *J. Mol. Biol.*, 350(4):806-816, 2005.

Escalona et al., *Nat Rev Genet.* 17(8): 459-469, 2016.

Espada and Martín-Pérez, *Int Rev Cell Mol Biol.* 331:83-122, 2017.

Gagnon-Arsenault, I., Tremblay, J., and Bourbonnais, Y. (2006) Fungal yapsins and cell wall: a unique family of aspartic peptidases for a distinctive cellular function, FEMS yeast research 6, 966-978.

Gal et al., *Curr. Opin. Struct. Biol.*, 17:467-473, 2007.

Gera et al., *Methods, Methods.* 60(1):15-26, 2013.

Girard, V., Dieryckx, C., Job, C., and Job, D. (2013) Secretomes: The fungal strike force, Proteomics 13, 597-608.

Gould and Tawfik, *Biochemistry*, 44(14):5444-5452, 2005.

Gray et al., *Cell*, 142(4):637-646, 2010.

Gupta et al., *Appl. Microbiol. Biotechnol.*, 59(1):15-32, 2002.

Han et al., *Appl. Environ. Microbiol.*, 78(9):3249, 2012.

Hedstrom, *Chem. Rev.*, 102(12):4501-4524, 2002.

Hegde and Keenan, *Nat Rev Mol Cell Biol.*, 12(12):787-98, 2011.

Hegde and Keenan, *Nat Rev Mol Cell Biol.*, 12(12):787-98, 2011.

Huang et al., *Genetics*, 182(1):173-89, 2009.

Jung et al., *Proc. Natl. Acad. Sci. U. S. A.*, 107:604-609, 2010.

Kapust et al., *Biochem. Biophys. Res. Commun.*, 294:949-955, 2002a.

Kim et al., *Anal. Biochem.*, 284(1):42-48, 2000.

Kim et al., *Appl Microbiol Biotechnol.*, 88(4):893-903, 2010.

Komano, H., Rockwell, N., Wang, G., Krafft, G., and Fuller, R. (1999) Purification and characterization of the yeast glycosylphosphatidylinositol-anchored, monobasic-specific aspartyl protease yapsin 2 (Mkc7p), The Journal of biological chemistry 274, 24431-24437.

Komano, H., Seeger, M., Gandy, S., Wang, G., Krafft, G., and Fuller, R. (1998) Involvement of cell surface glycosyl-phosphatidylinositol-linked aspartyl proteases in alpha-secretase-type cleavage and ectodomain solubilization of human Alzheimer beta-amyloid precursor protein in yeast, The Journal of biological chemistry 273, 31648-31651.

Kolaczkowska et al., FEBS Lett. Mar 19; 582(6): 977-983, 2008.

Kyte and Doolittle, *J. Mol. Biol.*, 157(1):105-132, 1982.

Ledgerwood, E., Brennan, S., Cawley, N., Loh, Y., and George, P. (1996) Yeast aspartic protease 3 (Yap3) prefers substrates with basic residues in the P2, P1 and P2' positions, FEBS letters 383, 67-71.

Lee et al., *Bioresource Tech.*, 102:9179-9184, 2011.

Levy et al. "Attacking a Moving Target: Understanding Resistance and Managing Progression in EGFR-Positive Lung Cancer Patients Treated With Tyrosine Kinase Inhibitors." *Oncology (Williston Park)*, 30(7):601-12, 2016.

Li et al. "Profiling Protease Specificity: Combining Yeast ER Sequestration Screening (YESS) with Next Generation Sequencing." *ACS Chem Biol.* 12(2):510-518, 2017.

Li, Q., Yi, L., Marek, P., and Iverson, B. (2013) Commercial proteases: present and future, FEBS letters 587, 1155-1163.

Lim et al., *J. Biol. Chem.*, 282(13):9722-9732, 2007.

Lin et al., *J. Immunol. Methods*, 375:159-165, 2012

Marnett and Craik, *Trends Biotechnol.*, 23(2):59-64, 2005.

Matthews, D., Goodman, L., Gorman, C., and Wells, J. (1994) A survey of furin substrate specificity using substrate phage display, Protein science: a publication of the Protein Society 3, 1197-1205.

MEROPS database (merops.sanger.ac.uk)

Mohanty et al., *Protein Expr. Purif.*, 27:109-114, 2003.

Monnat et al., *Molec. Biol. Cell*, 11:3469-3484, 2000.

Nallamsrtty et al., *Protein Expr. Purif.*, 38(1):108-15, 2004.

O'Donoghuel, A. J., Eroy-Reveles, A. A., Knudsen, G. M., Ingram, J., Zhoul, M., Statnekovl, Alexander, J. B., Greninger, L., Hostetterl, D. R., Qu, G., Maltby, D. A., Anderson, M. O., DeRisi, J. L., Burlingame, J. A, and Craik, C., (2012) Global Identification of Peptidase Specificity by Multiplex Substrate Profiling, Nat Methods 9, 1095-1100.

O'Loughlin et al., *Mol. Biol. Evol.*, 23(4):764-772, 2006.

Olsen, V., Cawley, N., Brandt, J., Egel-Mitani, M., and Loh, Y. (1999) Identification and characterization of Saccharomyces cerevisiae yapsin 3, a new member of the yapsin family of aspartic proteases encoded by the YPS3 gene, The Biochemical journal 339 (Pt 2), 407-411.

Overall and Blobel, *Nat. Rev. Mol. Cell Biol.*, 8(3):245-257, 2007.

Paltridge, J., Belle, L., and Khew-Goodall, Y. (2013) The secretome in cancer progression, Biochimica et biophysica acta.

Park and Rapoport, *Annu Rev Biophys.*, 41:21-40, 2012.

Pelham et al., *Embo J.*, 7(6):1757-1762, 1988.

Phan, J., Zdanov, A., Evdokimov, A., Tropea, J., Peters, H., Kapust, R., Li, M., Wlodawer, A., and Waugh, D. (2002) Structural basis for the substrate specificity of tobacco etch virus protease, The Journal of biological chemistry 277, 50564-50572.

Porro, D., Sauer, M., Branduardi, P., and Mattanovich, D. (2004) Recombinant protein production in yeasts, METHODS IN MOLECULAR BIOLOGY- . . . 31, 245-259.

Ramachandran et al., *Nat. Rev. Drug Discov.*, 11(1):69-86, 2012.

Rapoport, *Nature*, 450(7170):663-9, 2007.

Remington: The Science and Practice of Pharmacy, 21$^{st}$ Ed. Lippincott Williams and Wilkins, 2005.

Remington: The Science and Practice of Pharmacy, 21$^{st}$ Ed., Pharmaceutical Press, 2011.

Rockwell, N., and Fuller, R. (1998) Interplay between S1 and S4 subsites in Kex2 protease: Kex2 exhibits dual specificity for the P4 side chain, Biochemistry 37, 3386-3391.

Rockwell, N., Wang, G., Krafft, G., and Fuller, R. (1997) Internally consistent libraries of fluorogenic substrates demonstrate that Kex2 protease specificity is generated by multiple mechanisms, Biochemistry 36, 1912-1917.

Roebroek, A., Umans, L., Pauli, I., Robertson, E., van Leuven, F., Van de Ven, W., and Constam, D. (1998) Failure of ventral closure and axial rotation in embryos lacking the proprotein convertase Furin, Development (Cambridge, England) 125, 4863-4876.

Rozan, L., Krysan, D., Rockwell, N., and Fuller, R. (2004) Plasticity of extended subsites facilitates divergent substrate recognition by Kex2 and furin, The Journal of biological chemistry 279, 35656-35663.

Schechter and Berger, A *Biochem. Biophys. Res. Commun.*, 27(2):157-162, 1967.

Schilling and Overall, *Nat. Biotechnol.*, 26(6):685-694, 2008.

Scholle, M., Kriplani, U., Pabon, A., Sishtla, K., Glucksman, M., and Kay, B. (2006) Mapping protease substrates by using a biotinylated phage substrate library, Chembiochem: a European journal of chemical biology 7, 834-838.

Seidah, N., and Prat, A. (2002) Precursor convertases in the secretory pathway, cytosol and extracellular milieu, Essays in biochemistry 38, 79-94.

Sellamuthu et al., *Biochem. Biophys. Res. Commun.*, 371(1):122-126, 2008.

Sellamuthu et al., *PLoS One*, 6(7):e22554, 2011.

Semenza et al., *Cell*, 61(7):1349-1357, 1990.

Sinha, J., Plantz, B., Inan, M., and Meagher, M. (2005) Causes of proteolytic degradation of secreted recombinant proteins produced in methylotrophic yeast *Pichia pastoris*: case study with recombinant ovine interferon-tau, Biotechnology and bioengineering 89, 102-112.

Small et al., *Proteomics*, 4(6):1581-90, 2004.

Sudbery, P. (1996) The expression of recombinant proteins in yeasts, Current opinion in biotechnology 7, 517-524.

Teasdale and Jackson, *Cell Dev. Biol.* 12, 27-54, 1996.

Tropea et al., *Methods Mol. Biol.*, 498:297-307, 2009.

Varadarajan et al., *Angew. Chem. Int. Ed. Engl.*, 47(41): 7861-7863, 2008.

Varadarajan et al., *J. Am. Chem. Soc.*, 131(50):18186-18190, 2009a.

Varadarajan et al., *Nat. Chem. Biol.*, 4(5):290-294, 2008.

Varadarajan et al., *Nat. Protoc.*, 4(6):893-901, 2009b.

Varadarajan et al., *Proc. Natl. Acad. Sci. USA*, 102(19): 6855-6860, 2005.

Varkaris et al., *Cancer Metastasis Rev.* 33(2-3):595-606, 2014.

Villa et al., *J. Biol. Chem.*, 278(43):42545-42550, 2003.

Watanabe et al., *J Biosci Bioeng.* 89(6):569-76, 2000.

Waugh, *Protein Expr. Purif.*, 80:283-293, 2011.

Wehr et al., *Nat. Methods*, 3:985-993, 2006.

Yi et al. "Engineering of TEV protease variants by yeast ER sequestration screening (YESS) of combinatorial libraries." *Proc Natl Acad Sci USA.* 110(18):7229-34, 2013.

Yi et al., (2015) *Methods Mol Biol.* 1319:81-93.

Yi, L., Gebhard, M., Li, Q., Taft, J., Georgiou, G., and Iverson, B. (2013) Engineering of TEV protease variants by yeast ER sequestration screening (YESS) of combinatorial libraries, Proceedings of the National Academy of Sciences of the United States of America 110, 7229-7234.

Zhou, A., Webb, G., Zhu, X., and Steiner, D. (1999) Proteolytic processing in the secretory pathway, The Journal of biological chemistry 274, 20745-20748.

What is claimed is:

1. A method of measuring the presence or absence of drug resistance of a mutant kinase, comprising:
   (a) expressing in each of a plurality of eukaryotic cells:
      (i) a first fusion protein comprising an ER targeting sequence, a mutant kinase, and an ER retention sequence, wherein the mutant kinase comprises at least one point mutation relative to wild-type; and
      (ii) a vector encoding a second fusion protein comprising: an endoplasmic reticulum (ER) targeting sequence, a surface expression sequence, a first peptide sequence, and an endoplasmic reticulum (ER) retention sequence;
   wherein the eukaryotic cells are exposed to a kinase inhibitor during said expression wherein the kinase inhibitor is a tyrosine kinase inhibitor;
   (b) separating or purifying said eukaryotic cells based on the presence or absence of phosphorylation of at least one amino acid of the first peptide on the surface of the eukaryotic cells; wherein the presence or absence of phosphorylation is detected with an antibody, wherein the presence of phosphorylation indicates enzymatic activity of the mutant kinase, wherein enzymatic activity in the presence of the kinase inhibitor indicates resistance to the kinase inhibitor; and
   (c) sequencing the mutant kinase;
   wherein the mutant kinase is a tyrosine kinase.

2. The method of claim 1, wherein the kinase is at least partially randomized.

3. The method of claim 1, wherein the kinase is resistant to inhibition by the kinase inhibitor.

4. The method of claim 1, wherein the kinase is a Src kinase.

5. The method of claim 1, wherein the eukaryotic cell is a yeast.

6. The method of claim 5, wherein the yeast is a Kex2 (−/−) knockout yeast.

7. The method of claims 1, wherein the vector encodes a second fusion protein comprises in an N- to C- direction: an endoplasmic reticulum (ER) targeting sequence, a surface expression sequence, the first peptide sequence, and an endoplasmic reticulum (ER) retention sequence.

8. The method of claim 1, wherein the sequencing comprises next-generation sequencing.

9. The method of claim 8, wherein the next-generation sequencing comprises single-molecule real-time sequencing, an ion semiconductor method, a pyrosequencing method, a sequencing by synthesis method, or a sequencing by ligation method.

10. The method of claim 1, wherein the endoplasmic reticulum (ER) targeting sequence encoded in the vector is comprised in said surface expression sequence in the vector.

11. The method of claim 10, wherein the surface expression sequence is Aga2.

12. The method of claim 1, wherein the method further comprises repeating steps (a) and (b).

13. The method of claim 1, wherein said separating comprises fluorescence-activated cell sorting (FACS).

14. The method of claim 1, wherein the method comprises repeated FACS separation and culture of the eukaryotic cells.

15. The method of claim 14, wherein the enzyme is a kinase and wherein step (b) comprises FACS separation of cells via an antibody that selectively binds a phosphorylated amino acid.

16. The method of claim 15, wherein the phosphorylated amino acid is a tyrosine.

17. The method of claim 1, wherein the kinase is a human kinase.

18. The method of claim 17, wherein the kinase is a tyrosine kinase.

19. The method of claim 18, wherein the tyrosine kinase is a receptor tyrosine kinase.

20. The method of claim 18, wherein the tyrosine kinase is a non-receptor tyrosine kinase.

21. The method of claim 20, wherein the non-receptor tyrosine kinase is a Src kinase.

22. The method of claim 21, wherein the Src kinase is c-SRC, YES1, Fyn, Fgr, Lck, HCK, BTK, Blk, Lyn, or Frk.

23. The method of claim 20, wherein the kinase is ABL kinase, c-SRC, or Lyn.

24. The method of claim 1, wherein a first promoter controls expression of the first fusion protein, wherein the first promoter is expressable in yeast.

25. The method of claim 24, wherein the first promoter is Ga11, Ga110, or Ga14-BS2-pleum.

26. The method of claim 1, wherein the endoplasmic reticulum (ER) targeting sequence is MQLLRCFSIFSVI-ASVLA (SEQ ID NO:3).

27. The method of claim 1, wherein the endoplasmic reticulum (ER) retention sequence is FEHDEL (SEQ ID NO:4), KDEL (SEQ ID NO:5), HDEL (SEQ ID NO:6), or RDEL (SEQ ID NO:7).

28. The method of claim 1, wherein the purifying or separating comprises separating the cells based on the presence or absence of a first antibody that selectively binds a phosphorylated amino acid.

29. The method of claim 28, wherein the phosphorylated amino acid is a tyrosine.

30. The method of claim 29, wherein the antibody is labeled with a fluorophore.

31. The method of claim 29, wherein the purifying or separating comprises or consists of fluorescence activated cell sorting (FACS).

32. The method of claim 1, wherein the method further comprises an in vitro method for evaluating the risk of resistance to the kinase inhibitor in vivo.

33. The method of claim 32, wherein multiple resistant mutant kinases are generated and sequenced.

34. The method of claim 33, wherein the multiple mutant kinases are generated by error prone PCR.

35. The method of claim 33, wherein the multiple mutant kinases are generated by site directed mutagenesis.

36. The method of claim 32, wherein the multiple mutant kinases are obtained from a library.

37. The method of claim 32, wherein at least 1, 2, 3, 4, or 5 single mutations provide resistance to the kinase inhibitor.

38. The method of claim 32, wherein at least 1, 2, 3, 4, or 5 double mutations provide resistance to the kinase inhibitor.

39. The method of claim 32, wherein at least one of the multiple resistant kinases comprises a mutation that has been observed in a subject that is resistant to the kinase inhibitor in vivo.

40. The method of claim 33, wherein the mutations in the resistant mutant kinases are compared to a listing of mutations that can result in resistance to a second kinase inhibitor.

41. The method of claim 40, wherein the second kinase inhibitor has been approved for clinical use in vivo.

42. The method of claim 40, wherein the listing was obtained by sequencing kinases obtained from patients resistant to the second kinase inhibitor.

43. The method of claim 1, wherein the eukaryotic cell is a yeast, and wherein the yeast has one or more transporter genes knocked out.

44. The method of claim 43, wherein the yeast is a null mutant for 1, 2, or all of SNQ2, YOR1, and/or PDR5.

45. The method of claim 1, wherein the tyrosine kinase inhibitor is a Src kinase inhibitor.

* * * * *